(12) United States Patent
Aucott et al.

(10) Patent No.: US 10,481,165 B2
(45) Date of Patent: Nov. 19, 2019

(54) ELEVATED CCL19 AFTER COMPLETION OF THERAPY FOR ACUTE LYME DISEASE IDENTIFIES PATIENTS AT RISK FOR DEVELOPMENT OF POST-TREATMENT LYME DISEASE SYNDROME WHO WILL BENEFIT FROM FURTHER ANTIBIOTIC THERAPY

(71) Applicant: THE JOHNS HOPKINS UNIVERSITY, Baltimore, MD (US)

(72) Inventors: John N. Aucott, Lutherville, MD (US); Mark J. Soloski, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/058,316

(22) Filed: Aug. 8, 2018

(65) Prior Publication Data
US 2019/0178893 A1    Jun. 13, 2019

Related U.S. Application Data

(62) Division of application No. 15/131,063, filed on Apr. 18, 2016, now abandoned.

(60) Provisional application No. 62/148,332, filed on Apr. 16, 2015.

(51) Int. Cl.
| | | |
|---|---|---|
| A61K 31/43 | (2006.01) | |
| A61K 31/65 | (2006.01) | |
| G01N 33/68 | (2006.01) | |

(52) U.S. Cl.
CPC ......... *G01N 33/6863* (2013.01); *A61K 31/43* (2013.01); *A61K 31/65* (2013.01); *G01N 2333/43556* (2013.01); *G01N 2333/521* (2013.01); *G01N 2800/26* (2013.01); *G01N 2800/52* (2013.01); *G01N 2800/56* (2013.01); *Y02A 50/401* (2018.01); *Y02A 50/57* (2018.01)

(58) Field of Classification Search
None
See application file for complete search history.

(56) References Cited

PUBLICATIONS

Aucott et al. "Diagnostic challenges of early Lyme disease: lessons from a community case series" BMC Infect Dis. 2009; 9: 79.
Chandra et al. "Novel multiplex technology for diagnostic characterization of rheumatoid arthritis" Arthritis Res Ther. 2011; 13: R102.
Dandache et al. "Erythema migrans" Infect Dis Clin North Am. 2008; 22: 235-260.
Deane et al. "The number of elevated cytokines and chemokines in preclinical seropositive rheumatoid arthritis predicts time to diagnosis in an age-dependent manner" Arthritis Rheum. 2010; 62: 3161-3172.
Duray, P., "Histopathology of clinical phases of human lyme disease", Rheumatic Diseases Clinics of North America (1989) vol. 15, No. 4, pp. 691-710.
Hughes-Austin et al. "Multiple cytokines and chemokines are associated with rheumatoid arthritis-related autoimmunity in first-degree relatives without rheumatoid arthritis: Studies of the Aetiology of Rheumatoid Arthritis (SERA)" Ann Rheum Dis. 2013; 72: 901-907.
Jones et al. "Higher mRNA levels of chemokines and cytokines associated with macrophage activation in erythema migrans skin lesions in patients from the United States than in patients from Austria with Lyme borreliosis" Clin Infect Dis. 2008; 46: 85-92.
Lindstrom et al. "Biomarkers for rheumatoid arthritis: making it personal" Scand J Clin Lab Invest Suppl. 2010; 242: 79-84.
Mullegger et al. "Chemokine signatures in the skin disorders of Lyme borreliosis in Europe: predominance of CXCL9 and CXCL10 in erythema migrans and acrodermatitis and CXCL13 in lymphocytoma" Infect Immun. 2007; 75: 4621-4628.
Shin et al. "High levels of inflammatory chemokines and cytokines in joint fluid and synovial tissue throughout the course of antibiotic-refractory lyme arthritis" Arthritis Rheum. 2007; 56: 1325-1335.
Steere. "Lyme disease" N Engl J Med. 2001; 345: 115-125.
Steere et al. "Elucidation of Lyme arthritis" Nat Rev Immunol. 2004; 4: 143-152.
Strle et al. "Borrelia burgdorferi RST1 (OspC type A) genotype is associated with greater inflammation and more severe Lyme disease" Am J Pathol. 2011; 178: 2726-2739.
Strle et al. "Association of a Toll-like receptor 1 polymorphism with heightened Th1 inflammatory responses and antibiotic-refractory Lyme arthritis" Arthritis Rheum. 2012; 64: 1497-1507.
Wormser et al. "The clinical assessment, treatment, and prevention of lyme disease, human granulocytic anaplasmosis, and babesiosis: clinical practice guidelines by the Infectious Diseases Society of America" Clin Infect Dis. 2006; 43: 1089-1134.
Soloski, M., et al., "Serum Inflammatory Mediators as Markers of Human Lyme Disease Activity" PLoS ONE (2014) vol. 9, No. 4, e93243. doi:10.1371/journal.pone.0093243.
Rupprecht, et al., "The chemokine CXCL13 is a key regulator of B cell recruitment to the cerebrospinal fluid in acute Lyme neuroborreliosis" Journal of Neuroinflammation (2009) vol. 6, No. 42.

*Primary Examiner* — Jared Barsky
(74) *Attorney, Agent, or Firm* — Johns Hopkins Technology Ventures

(57) ABSTRACT

The present invention relates to the field of Lyme disease. More specifically, the present invention provides methods and composition useful for the treatment of Lyme disease. In one aspect, the present invention provides compositions and methods for treating a patient at risk for or likely to develop post-treatment Lyme disease syndrome (PTLDS). In certain embodiments, the patient is already undergoing a first course of antibiotic treatment for Lyme disease. In a specific embodiment, a method comprises the step of prescribing or administering a second course of antibiotic treatment to a patient who is determined to have an increased level of CCL19 as compared to a control after completing a first course of antibiotics for Lyme disease.

2 Claims, 11 Drawing Sheets

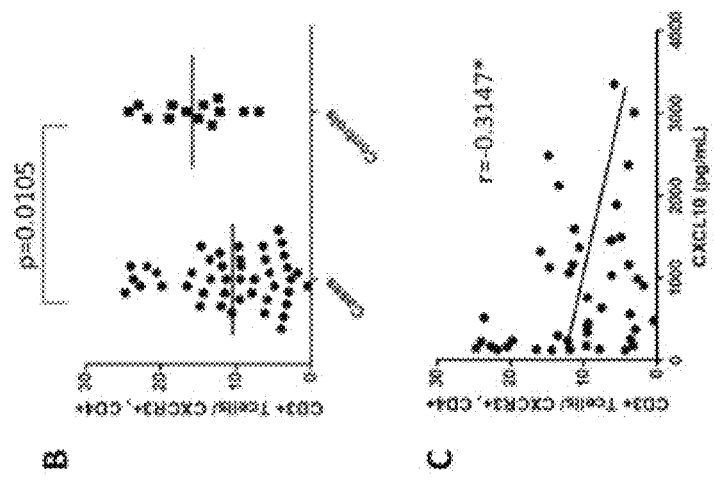
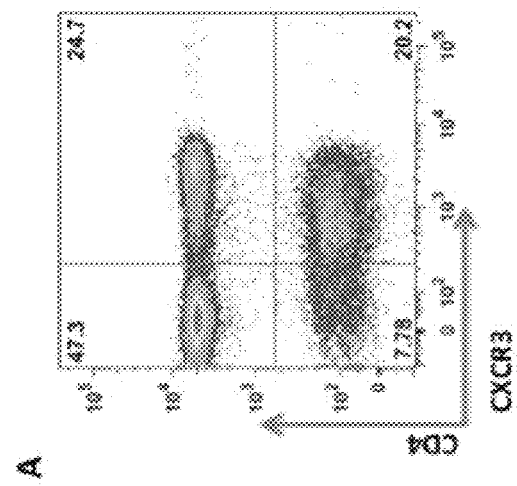
FIG. 6B
FIG. 6C
FIG. 6A

ELEVATED CCL19 AFTER COMPLETION OF THERAPY FOR ACUTE LYME DISEASE IDENTIFIES PATIENTS AT RISK FOR DEVELOPMENT OF POST-TREATMENT LYME DISEASE SYNDROME WHO WILL BENEFIT FROM FURTHER ANTIBIOTIC THERAPY

CROSS-REFERENCE TO RELATED APPLICATIONS

This application is a Divisional of U.S. patent application Ser. No. 15/131,063, filed Apr. 18, 2016, which claims the benefit of U.S. Provisional Application No. 62/148,332, filed Apr. 16, 2015, to content of each of the aforementioned applications is here incorporated herein by reference in their entirety.

FIELD OF THE INVENTION

The present invention relates to the field of Lyme disease. More specifically, the present invention provides methods and composition useful for the treatment of Lyme disease.

BACKGROUND OF THE INVENTION

Lyme disease is the most common tick-borne disease in temperate regions of the northern hemisphere, affecting large areas of North America and Eurasia.[1] In North America, Lyme disease is caused by the spirochete *Borrelia burgdorferi* and cases are concentrated in the Northeast, upper Midwest and Mid-Atlantic. Recently, CDC and state health investigators estimated that 288,000 new infections occurred in the United States in 2008.[2] In certain high-risk communities, studies suggest that the incidence of new cases may be 3%, with cumulative prevalence as high as 7-17%.[3] As the geographic range of the tick vector, and the mouse and deer hosts expands, the impact of Lyme and other tick borne-diseases is likely to grow.[4]

The hallmark of early Lyme disease is a cutaneous lesion, erythema migrans (EM), which occurs with or without symptoms of infection such as fever, arthralgias, fatigue, headache or neck pain.[5] Within days to weeks, *B. burgdorferi* may disseminate from the site of skin inoculation through the blood or tissues and spread systemically to other areas of the skin, musculoskeletal, cardiac and neurologic systems. More than 50% of patients with EM are found to have positive PCR or blood culture results at this stage.[6, 7] In the absence of effective antibiotic treatment, the adaptive immune response does not reliably eradicate infection, with small numbers of spirochetes able to persist in certain tissues.[8] If untreated, as many as 60% of patients will have a clinical relapse months to years later with manifestations of late Lyme arthritis or less commonly in the United States, neurologic disease.[9]

Antibiotic treatment of early Lyme disease speeds resolution of EM and is effective in preventing later objective manifestations. However, treatment at later stages may be more difficult. Approximately 10% of late Lyme arthritis patients have persistent or recurrent objective findings termed post-treatment antibiotic refractory disease. This is thought to be due to autoimmune-mediated inflammation that occurs in genetically susceptible individuals, especially those with Toll-like receptor 1 polymorphism and/or the HLA-DR4 alleles.[10]

Approximately 10% of patients with diagnosed and treated early Lyme disease have persistent symptoms of fatigue, arthralgias, sleep disruption or cognitive complaints following antibiotic treatment. These post-treatment symptoms may be mild and limited, or severe and chronic. When post-treatment symptoms last six months or longer and impair life functioning, patients meet the case definition for post-treatment Lyme disease syndrome (PTLDS).[1, 11, 12] Studies have suggested a severe initial illness,[13, 14] delayed treatment,[13] neurologic involvement,[1, 15] or suboptimal antibiotic therapy [15, 16] as potential risk factors for development of PTLDS.

The pathophysiology of PTLDS is unknown, but theories include persistence of bacteria and/or spirochetal antigens after antibiotic therapy, as suggested by animal models.(18, 19) Immune system abnormalities independent of ongoing infection may also be an important mechanism. Retained spirochetal antigens have been hypothesized to lead to immune dysregulation of $CD4^+$ T cell subsets in antibiotic refractory arthritis.[19] Anti-neural antibodies have been found in one sample of patients with PTLDS.[20]

As described below, we examined serum levels of sixty-five immune mediators among patients with acute Lyme disease and identified a clear associated signature relative to normal controls, including increased CXCL9, CXCL10, and CCL19.[21] We then sought to examine the relationship of these immune mediators to patient clinical response over time, from pre-treatment diagnosis of early Lyme disease up to one year following completion of antibiotic treatment. We hypothesize that those individuals who meet the case definition of PTLDS, as compared to those that don't meet criteria and normal controls, will have persistent elevations of specific immune mediators following antibiotic treatment.

SUMMARY OF THE INVENTION

The present invention is based, at least in part, on the discovery the chemokine CCL19 has been identified in acute pre-treatment samples from patients with Lyme disease and distinguishes acutely infected patients from controls. In addition we have demonstrated that a subset of patient continue to have elevated levels of CCL19 for up to 6-12 months post-treatment. In addition, the measurement of an elevated CCL19 immediately after the completion of antibiotic therapy identifies those at high risk of having persistent symptoms. This high risk population is a candidate for further antibiotic therapy to prevent the development of long term complications of PTLDS.

No previous investigators have described persistent elevations of CCL19 in patients after treatment of Lyme disease and have not linked CCL19 elevation to the risk for PTLDS. No one has suggested that this biomarker could be used to identify a subset of patients requiring repeat or prolonged antibiotic therapy in an attempt to prevent the development of PTLDS. Indeed, the present inventors are the first to link the CCL19 patterns before and after treatment of Lyme disease to the clinical phenotype of Post-treatment Lyme disease syndrome.

Accordingly, in one aspect, the present invention provides compositions and methods for treating a patient at risk for or likely to develop post-treatment Lyme disease syndrome (PTLDS). In certain embodiments, the patient is already undergoing a first course of antibiotic treatment for Lyme disease. In a specific embodiment, a method comprises the step of prescribing or administering a second course of antibiotic treatment to a patient who is determined to have an increased level of CCL19 as compared to a control after completing a first course of antibiotics for Lyme disease. In certain embodiments, the second course of antibiotics comprises an antibiotic that is different from the first course of antibiotics.

In another embodiment, a method for treating a patient likely to develop PTLDS comprises the steps of (a) obtaining a biological sample from a patient being treated for Lyme disease with a first course of antibiotics; (b) measuring the level of CCL19 in the sample; and (c) prescribing or administering a second course of antibiotic treatment to a patient having an increased level of CCL19 as compared to a control.

In a further embodiment, a method comprising the steps of (a) measuring the level of CCL19 in a serum sample obtained from a patient undergoing a first antibiotic treatment for Lyme disease; and (b) generating a report comprising the measured CCL19 level. In a specific embodiment, the report further comprises standard or control levels of CCL19 for comparison. The report can further comprise a treatment recommendation based on the measured level of CCL19.

In yet another embodiment, the present invention provides a method comprising the steps of (a) measuring the level of CCL19 in a serum sample obtained from a patient undergoing a first antibiotic treatment for Lyme disease; and (b) recommending a second course of antibiotic treatment to treat or prevent PTLDS if the measure level of CCL19 is statistically significantly increased as compared to a reference or control.

In particular embodiments, levels of CCL19 are statistically significantly increased if the levels are 2 standard deviations above the control. In certain embodiments, the cutoff is ≥182 pg/mL.

In further embodiments, the methods described herein further comprise measuring the levels of one or more biomarkers described herein. The biomarkers described herein, including CCL19, can be measured using the techniques described herein including, but not limited to, immunoassay and mass spectrometry. In particular embodiments, the biomarkers, including CCL19, are detected and measured using a multiplex assay system such as the Bio-Plex® Multiplex System (Bio-Rad Laboratories, Inc. (Hercules, Calif.)).

In further embodiments, the present invention provides methods for treating a patient who continues to have elevated biomarker levels, including CCL19, after the antibiotic retreatment. In a specific embodiment, the method further comprises recommending, prescribing or administering an immunomodulator or immunosuppressive therapy. Examples include, but are not limited to, low dose allergy (LDA) therapy/low dose immunotherapy (LDI). In other embodiments, a therapeutic that blocks CCL19 production, pathway or acts as a CCL19 antagonist could be used. In another specific embodiment, a rheumatic drug like hydroxychloroquine is used.

BRIEF DESCRIPTION OF THE FIGURES

FIG. 1A. Results are displayed as a heat map to visualize differences in mediator levels in Acute Lyme patients relative to controls. FIG. 1B. Unsupervised hierarchical clustering of the results was performed, and the output displayed as a heat map. This analysis resulted in the formation of two clusters, including a "mediator high" cluster that contains samples derived from patients with acute *B. burgdorferi* infection who exhibited elevated serum inflammatory mediators. The second "mediator low" cluster includes a subset of samples from acute *B. burgdorferi* infection as well as the matched healthy controls, both of which exhibited low levels of inflammatory mediators.

FIG. 6A-6C. CXCR3 Expressing CD4+ T cell levels correlate with serum CXCL10. FIG. 6A. CXCR3 expressing CD4+ T cells were detected using polychromatic flow cytometry. Displayed is a representative plot. FIG. 6B. The frequency of CXCR3+CD4+ T cells among total CD4+ PBMCs were determined in Lyme patients prior to treatment (cases, n=44) and healthy controls (n=23). Levels of CXCR3+CD4+ T cells were lower in cases vs. controls at pre-treatment (p=0.0105). FIG. 6C. The levels of blood CXCR3+CD4+ T cells were negatively correlated CXCL10 serum levels in pretreatment early Lyme disease cases (p=0.0375).

FIG. 7A shows those mediators with significant changes (q<0.1%) in Lyme patients compared to controls at six months post-treatment. FIG. 7B shows significant differences in CCL19 levels between Lyme-exposed PTLDS patients and Lyme-exposed non-PTLDS patients at three months post-treatment.

DETAILED DESCRIPTION OF THE INVENTION

Figure 1A:
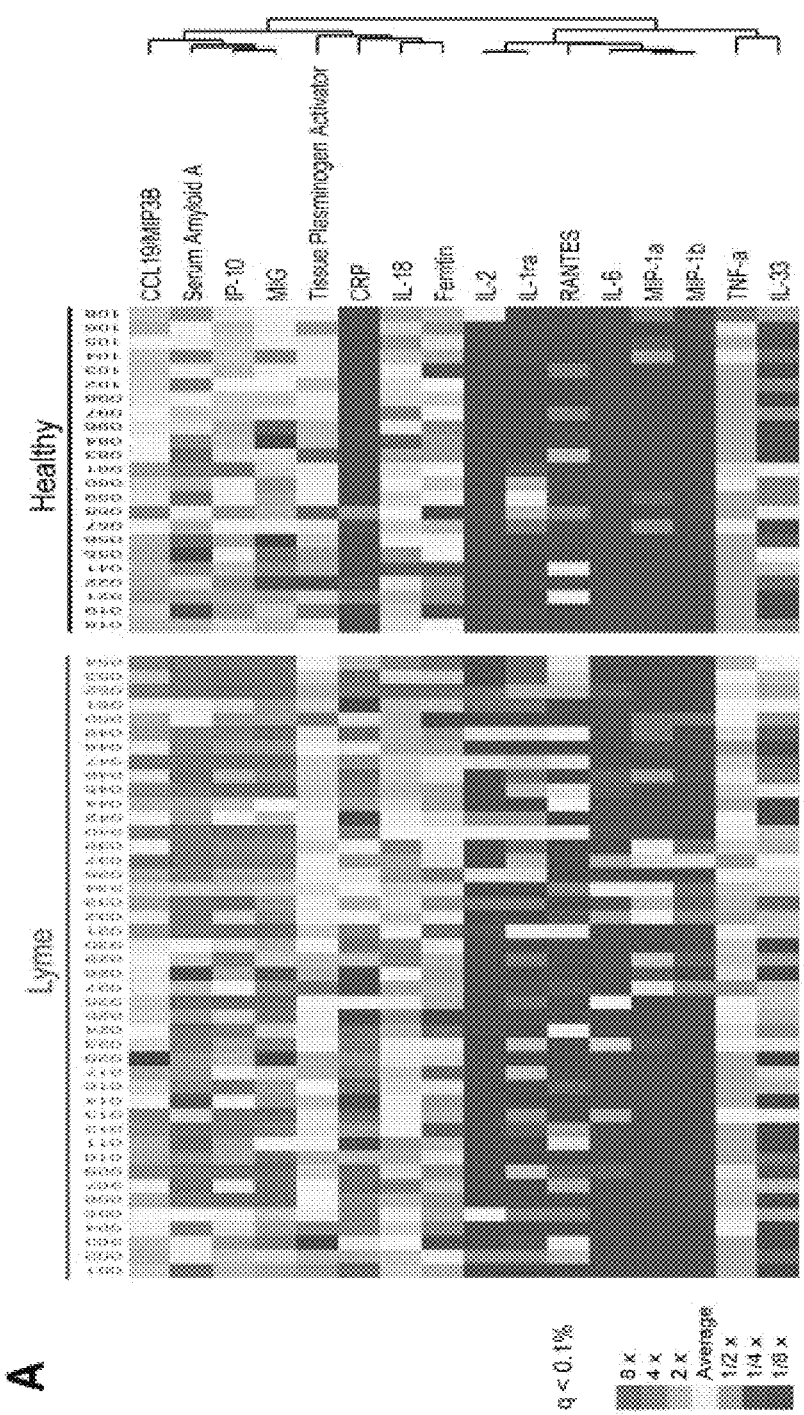
FIG. 1A-1B. Elevated Immune Mediators in Lyme Disease. Serum samples from patients with diagnosed acute Lyme disease (n=44, red) and healthy controls (n=23, black) were assayed for the presence of 58 soluble mediators and 7 acute phase proteins using an optimized multiplex-based assay system. Displayed are those mediators that show significant changes (q,0.1%) in Lyme patients vs. controls.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies.

As used herein, the term "antigen" is generally used in reference to any substance that is capable of reacting with an antibody. More specifically, as used herein, the term "antigen" refers to a biomarker described herein. An antigen can also refer to a synthetic peptide, polypeptide, protein or fragment of a polypeptide or protein, or other molecule which elicits an antibody response in a subject, or is recognized and bound by an antibody.

As used herein, the term "biomarker" refers to a molecule that is associated either quantitatively or qualitatively with a biological change. Examples of biomarkers include proteins, polypeptides, and fragments of a polypeptide or protein; and polynucleotides, such as a gene product, RNA or RNA fragment. In particular embodiments, a biomarker is a cytokine. In certain embodiments, a "biomarker" means a molecule/compound that is differentially present (i.e., increased or decreased) in a biological sample as measured/compared against the same marker in another biological sample or control/reference. In other embodiments, a biomarker can be differentially present in a biological sample as measured/compared against the other markers in same or another biological sample or control/reference. In further embodiments, one or more biomarkers can be differentially present in a biological sample as measured/compared against other markers in the same or another biological sample or control/reference and against the same markers in another biological sample or control/reference. In yet another embodiment, a biomarker can be differentially present in a biological sample from a subject or a group of subjects having a first phenotype (e.g., having a disease or condition) as compared to a biological sample from a subject or group of subjects having a second phenotype (e.g., not having the disease or condition or having a less severe version of the disease or condition).

In general, the one or more biomarkers can be generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using, for example, either Welch's T-test or Wilcoxon's rank-sum Test). Biomarker levels can be used in conjunction with other parameters to assess a patient.

As used herein, the term "comparing" refers to making an assessment of how the proportion, level or cellular localization of one or more biomarkers in a sample from a patient relates to the proportion, level or cellular localization of the corresponding one or more biomarkers in a standard, reference or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard, reference or control sample. In particular embodiments, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, having or not having or is likely (or not) of developing PTLDS. In another specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to having or having a likelihood (or not) of developing PTLDS.

In another embodiment, the term "comparing" refers to making an assessment of how the proportion, level or cellular localization of one or more biomarkers in a sample from a patient relates to the proportion, level or cellular localization of one or more biomarkers in the same sample. For example, a ratio of one biomarker to another (or more) from the same patient sample can be compared. Percentages or ratios of expression or levels of the biomarkers can be compared to other percentages or ratios in the same sample and/or to predefined reference or control percentages or ratios. Such comparison can be made to assess whether the patient has or does not have or is likely (or not) of developing PTLDS, which assessment can be used to direct further therapy.

In embodiments in which the relationship of the biomarkers are described in terms of a ratio, the ratio can include 1-fold, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, 100-fold or more difference (higher or lower). Alternatively, the difference can include 0.9-fold, 0.8-fold, 0.7-fold, 0.7-fold, 0.6-fold, 0.5-fold, 0.4-fold, 0.3-fold, 0.2-fold, and 0.1-fold (higher or lower) depending on context. The foregoing can also be expressed in terms of a range (e.g., 1-5 fold/times higher or lower) or a threshold (e.g., at least 2-fold/times higher or lower).

The evaluation of the relationship between one or more biomarkers in a sample (e.g., one or more biomarkers compared to one or more other biomarkers (perhaps in combination with internal standards expression or levels (e.g., actin)) can also be expressed in terms of a percentage including, but not limited to, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200% or more (higher or lower) difference. The foregoing can also be expressed in terms of a range (e.g., 50-100% higher or lower) or a threshold (e.g., at least 50% higher or lower)

As used herein, the terms "identifies," "indicates" or "correlates" (or "identifying," "indicating" or "correlating," or "identification," "indication" or "correlation," depending on the context) in reference to a parameter, e.g., a modulated proportion, level, or cellular localization in a sample from a patient, may mean that the patient has or does not have or is likely (or not) of developing PTLDS. In specific embodiments, the parameter may comprise the level (expression level or protein level) of one or more biomarkers of the present invention. A particular set or pattern of the amounts of one or more biomarkers may identify the patient as having or not having or being likely (i.e., at risk) (or not) of developing PTLDS.

In certain embodiments, "identifying," "indicating," or "correlating," as used according to the present invention, may be by any linear or non-linear method of quantifying the relationship between levels/ratios of biomarkers to other biomarkers and/or standard, control or comparative value for the assessment of Lyme disease/PTLDS.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The terms are also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of Lyme disease and/or PTLDS. Moreover, a sample obtained from a patient can be divided and only a portion may be used for diagnosis. Further, the sample, or a portion thereof, can be stored under conditions to maintain sample for later analysis. The definition specifically encompasses solid tissue samples such as a biopsy specimen or tissue cultures or cells derived therefrom and the progeny thereof. In other embodiments, the term sample includes blood and other liquid samples of biological origin (including, but not limited to, peripheral blood, serum, plasma, cerebrospinal fluid, urine, saliva, stool and synovial fluid). In particular embodiments, the biological sample is a serum sample.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological samples, prepared for pathological analysis or study by immunohistochemistry. In certain embodiments, a sample comprises an optimal cutting temperature (OCT)-embedded frozen tissue sample.

As used herein, the term "predetermined threshold value" of a biomarker refers to the level of the same biomarker in a corresponding control/normal sample or group of control/ normal samples. Further, the term "altered level" of a biomarker in a sample refers to a level that is either below or above the predetermined threshold value for the same biomarker and thus encompasses either high (increased) or low (decreased) levels.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, lectins, proteins and antibodies, such as monoclonal or polyclonal antibodies, or antigen-binding fragments thereof, aptamers, etc. In certain embodiments, a binding agent binds a biomarker with an affinity constant of, for example, greater than or equal to about $1 \times 10^{-6}$ M. A binding agent can also comprise a probe or primer that specifically hybridizes a biomarker nucleic acid.

The terms "specifically binds to," "specific for," and related grammatical variants refer to that binding which occurs between such paired species as enzyme/substrate, receptor/agonist, antibody/antigen, nucleic acid/complement and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Various methodologies of the instant invention include a step that involves comparing a value, level, feature, characteristic, property, etc. to a "suitable control," referred to interchangeably herein as an "appropriate control," a "control sample" or a "reference." A "suitable control," "appropriate control," "control sample" or a "reference" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control cell, organ, or patient, exhibiting, for example, a particular disease state (e.g., Lyme disease, PTLDS, etc.) or lack thereof. In another embodiment, a "suitable control" or "appropriate control" is a value, level, feature, characteristic, property, ratio, etc. (e.g., biomarker levels that correlate to a particular phenotype) determined prior to performing a therapy (e.g., Lyme disease treatment) on a patient. In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control," "appropriate control" or a "reference" is a predefined value, level, feature, characteristic, property, ratio, etc. A "suitable control" can be a profile or pattern of levels/ratios of one or more biomarkers of the present invention that correlates to a particular phenotype (e.g., having or is likely to develop PTLDS) to which a patient sample can be compared. The patient sample can also be compared to a negative control. Such reference levels may also be tailored to specific techniques that are used to measure levels of biomarkers in biological samples (e.g., LC-MS, GC-MS, ELISA, PCR, etc.), where the levels of biomarkers may differ based on the specific technique that is used. In particular embodiments, a control or reference can be a profile or pattern of levels of one or more biomarkers that correlates having or not having or likely (or not) of developing PTLDS.

II. Binding Agents

A binding agent is an agent that binds to a biomarker. The binding agent can be a capture agent, and the terms can be used interchangeably as the context indicates. For example, the capture agent can be a capture antibody that binds to an antigen on the biomarker. The capture agent can be coupled to a substrate and used to isolate the biomarker.

A binding agent can be DNA, RNA, monoclonal antibodies, polyclonal antibodies, Fabs, Fab', single chain antibodies, synthetic antibodies, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), dendrimers, or combinations thereof. For example, the binding agent can be a capture antibody.

In some instances, a single binding agent can be employed to isolate a biomarker. In other instances, a combination of different binding agents may be employed to isolate a biomarker. For example, at least 2, 3, 4, 5, 6, 7, 8, 9, 10, 11, 12, 13, 14, 15, 16, 17, 18, 19, 20, 25, 50, 75 or 100 different binding agents may be used to isolate a biomarker from a biological sample.

Different binding agents can also be used for multiplexing. For example, isolation of more than biomarker can be performed by isolating each biomarker with a different binding agent. Different binding agents can be bound to different particles, wherein the different particles are labeled. In another embodiment, an array comprising different binding agents can be used for multiplex analysis, wherein the different binding agents are differentially labeled or can be ascertained based on the location of the binding agent on the array. Multiplexing can be accomplished up to the resolution capability of the labels or detection method, such as described below.

The binding agent can be an antibody. For example, a biomarker may be isolated using one or more antibodies specific for one or more antigens present on the biomarker. The antibodies can be immunoglobulin molecules or immunologically active portions of immunoglobulin molecules, i.e., molecules that contain an antigen binding site that specifically binds an antigen and synthetic antibodies. The immunoglobulin molecules can be of any class (e.g., IgG, IgE, IgM, IgD or IgA) or subclass of immunoglobulin molecule. Antibodies include, but are not limited to, polyclonal, monoclonal, bispecific, synthetic, humanized and chimeric antibodies, single chain antibodies, Fab fragments and F(ab')2 fragments, Fv or Fv' portions, fragments produced by a Fab expression library, anti-idiotypic (anti-Id) antibodies, or epitope-binding fragments of any of the above. An antibody, or generally any molecule, "binds specifically" to an antigen (or other molecule) if the antibody binds preferentially to the antigen, and, e.g., has less than about 30%, 20%, 10%, 5% or 1% cross-reactivity with another molecule.

The binding agent can also be a polypeptide or peptide. Polypeptide is used in its broadest sense and may include a sequence of subunit amino acids, amino acid analogs, or peptidomimetics. The subunits may be linked by peptide bonds. The polypeptides may be naturally occurring, processed forms of naturally occurring polypeptides (such as by enzymatic digestion), chemically synthesized or recombinantly expressed. The polypeptides for use in the methods of the present invention may be chemically synthesized using standard techniques. The polypeptides may comprise D-amino acids (which are resistant to L-amino acid-specific proteases), a combination of D- and L-amino acids, β amino acids, or various other designer or non-naturally occurring amino acids (e.g., β-methyl amino acids, Cα-methyl amino acids, and Nα-methyl amino acids, etc.) to convey special properties. Synthetic amino acids may include ornithine for lysine, and norleucine for leucine or isoleucine. In addition, the polypeptides can have peptidomimetic bonds, such as ester bonds, to prepare polypeptides with novel properties. For example, a polypeptide may be generated that incorporates a reduced peptide bond, i.e., $R_1-CH_2-NH-R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. Polypeptides can also include peptoids (N-substituted glycines), in which the side chains are appended to nitrogen atoms along the molecule's backbone, rather than to the a-carbons, as in amino acids. Polypeptides and peptides are intended to be used interchangeably throughout this application, i.e., where the term peptide is used, it may also include polypeptides and where the term polypeptides is used, it may also include peptides.

A binding agent can also be linked directly or indirectly to a solid surface or substrate. A solid surface or substrate can be any physically separable solid to which a binding agent can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, TEFLON®, etc.), polysaccharides, nylon or nitrocellulose, resins, silica or silica-based materials including silicon and modified silicon, carbon, metals, inorganic glasses, plastics, ceramics, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In addition, as is known the art, the substrate may be coated using passive or chemically-derivatized coatings with any number of materials, including polymers, such as dextrans, acrylamides, gelatins or agarose. Such coatings can facilitate the use of the array with a biological sample.

For example, an antibody used to isolate a biomarker can be bound to a solid substrate such as a well, such as commercially available plates. Each well can be coated with the antibody. In some embodiments, the antibody used to isolate a biomarker can be bound to a solid substrate such as an array. The array can have a predetermined spatial arrangement of molecule interactions, binding islands, biomolecules, zones, domains or spatial arrangements of binding islands or binding agents deposited within discrete boundaries. Further, the term array may be used herein to refer to multiple arrays arranged on a surface, such as would be the case where a surface bore multiple copies of an array. Such surfaces bearing multiple arrays may also be referred to as multiple arrays or repeating arrays.

A binding agent can also be bound to particles such as beads or microspheres. For example, an antibody specific for a biomarker can be bound to a particle, and the antibody-bound particle is used to isolate biomarkers from a biological sample. In some embodiments, the microspheres may be magnetic or fluorescently labeled. In addition, a binding agent for isolating biomarkers can be a solid substrate itself. For example, latex beads, such as aldehyde/sulfate beads (Interfacial Dynamics, Portland, Oreg.) can be used.

A binding agent bound to a magnetic bead can also be used to isolate a biomarker. For example, a biological sample such as serum from a patient can be collected for Lyme/PTLDS screening. The sample can be incubated with an antibody to a biomarker coupled to magnetic microbeads. A low-density microcolumn can be placed in the magnetic field of a MACS Separator and the column is then washed with a buffer solution such as Tris-buffered saline. The magnetic immune complexes can then be applied to the column and unbound, non-specific material can be discarded. The selected biomarkers can be recovered by removing the column from the separator and placing it on a collection tube. A buffer can be added to the column and the magnetically labeled biomarkers can be released by applying the plunger supplied with the column. The isolated biomarkers can be diluted in IgG elution buffer and the complex can then be centrifuged to separate the microbeads from the biomarkers. The pelleted isolated cell-of-origin specific biomarkers can be resuspended in buffer such as phosphate-buffered saline and quantitated. Alternatively, due to the strong adhesion force between the antibody captured cell-of-origin specific biomarkers and the magnetic microbeads, a proteolytic enzyme such as trypsin can be used for the release of captured biomarkers without the need for centrifugation. The proteolytic enzyme can be incubated with the antibody captured cell-of-origin specific biomarkers for at least a time sufficient to release the biomarkers.

A binding agent, such as an antibody, for isolating a biomarker is preferably contacted with the biological sample comprising the biomarker of interest for at least a time sufficient for the binding agent to bind to the biomarker. For example, an antibody may be contacted with a biological sample for various intervals ranging from seconds to hours to days, including but not limited to, about 1, 2, 3, 4, 5, 6, 7, 8, 9, 10, 11, 12, 13, 14, 15, 16, 17, 18, 19. 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more minutes, 1, 2, 3, 4, 5, 6, 7, 8, 9, 10, 11, 12, 13, 14, 15, 16, 17, 18, 19. 20, 21, 22, 23, 24 or more hours, 1 day, 3 days, 7 days or 10 days.

A binding agent, such as an antibody specific to a biomarker described herein can be labeled with, but is not limited to, a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles. The label can be, but not be limited to, fluorophores, quantum dots, or radioactive labels. For example, the label can be a radioisotope (radionuclides), such as $^{3}$H, $^{11}$C, $^{14}$C, $^{18}$F, $^{32}$F, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{3177}$Lu, $^{211}$At, or $^{213}$Bi. The label can be a fluorescent label, such as a rare earth chelate (europium chelate), fluorescein type, such as, but not limited to, FITC, 5-carboxyfluorescein, 6-carboxy fluorescein; a rhodamine type, such as, but not limited to, TAMRA; dansyl; Lissamine; cyanines; phycoerythrins; Texas Red; and analogs thereof.

A binding agent can be directly or indirectly labeled, e.g., the label can be attached to the antibody through biotin-streptavidin. Alternatively, an antibody is not labeled, but is later contacted with a second antibody that is labeled after the first antibody is bound to an antigen of interest.

For example, various enzyme-substrate labels are available or disclosed (see for example, U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, but are not limited to, horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and .beta.-D-galactosidase (β-D-Gal) with a chromogenic substrate (e.g., p-nitrophenyl-β-D-galactosidase) or fluorogenic substrate 4-methylumbelliferyl-β-D-galactosidase.

Depending on the method of isolation used, the binding agent may be linked to a solid surface or substrate, such as arrays, particles, wells and other substrates described above. Methods for direct chemical coupling of antibodies, to the cell surface are known in the art, and may include, for example, coupling using glutaraldehyde or maleimide activated antibodies. Methods for chemical coupling using multiple step procedures include biotinylation, coupling of trinitrophenol (TNP) or digoxigenin using for example succinimide esters of these compounds. Biotinylation can be accomplished by, for example, the use of D-biotinyl-N-hydroxysuccinimide. Succinimide groups react effectively with amino groups at pH values above 7, and preferentially between about pH 8.0 and about pH 8.5. Biotinylation can be accomplished by, for example, treating the cells with dithiothreitol followed by the addition of biotin maleimide.

III. Detection of Lyme/PTLDS Biomarkers

A. Detection by Immunoassay

In other embodiments, the biomarkers of the present invention can be detected and/or measured by immunoassay. Immunoassay requires biospecific binding reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds a biomarker and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample can comprise contacting the biological sample with one or more binding/capture agents (e.g., antibodies, peptides, aptamer, etc., combinations thereof) to form a biomarker:binding agent complex. The complexes can then be detected and/or quantified. A subject can then be identified as having (or not) or likely (or not) to develop PTLDS based on a comparison of the detected/quantified/measured levels of biomarkers to one or more reference controls as described herein.

In certain embodiments, the levels of the biomarkers employed herein are quantified by immunoassay, such as enzyme-linked immunoassay (ELISA) technology. In specific embodiments, the levels of expression of the biomarkers are determined by contacting the biological sample with antibodies, or antigen binding fragments thereof, that selectively bind to the biomarkers; and detecting binding of the antibodies, or antigen binding fragments thereof, to the biomarkers. In certain embodiments, the binding agents employed in the disclosed methods and compositions are labeled with a detectable moiety. For ease of reference, the term antibody is used in describing binding agents or capture molecules. However, it is understood that reference to an antibody in the context of describing an exemplary binding agent in the methods of the present invention also includes reference to other binding agents including, but not limited to lectins, peptides, aptamers and small organic molecules.

Furthermore, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. Kits for the detection of biomarkers as described herein can include pre-coated strip plates, biotinylated secondary antibody, standards, controls, buffers, streptavidin-horse radish peroxidise (HRP), tetramethyl benzidine (TMB), stop reagents, and detailed instructions for carrying out the tests including performing standards.

The present disclosure also provides methods in which the levels of the biomarkers in a biological sample are determined simultaneously. For example, in one embodiment, methods are provided that comprise: (a) contacting a biological sample obtained from the subject with a plurality of binding agents that selectively bind to a plurality of biomarkers disclosed herein for a period of time sufficient to form binding agent-biomarker complexes; and (b) detecting binding of the binding agents to the plurality of biomarkers, thereby determining the levels of the biomarkers in the biological sample. In a further embodiment, the method further comprises comparing the determined levels to a control or reference sample. In other embodiments, the method can further comprise generating a report summarizing the biomarker levels. In other embodiments, the method may further comprise recommending a particular treatment. For example, biomarker levels that are stastistically significantly above or below control/reference levels indicates that the subject should be treated with one or more treatment modalities appropriate for a subject having or likely to have (i.e., at risk of) PTLDS. For example, the current Infectious Disease Society of America guidelines recommend 10 days to 3 weeks of doxycycline or amoxicillin. Guidelines specifically discourage re-treatment with antibiotics based on persistent symptoms alone. In particular embodiments, if patients had elevated CC119 (especially if still symptomatic) then they should be prescribed/administered a repeat course of a different antibiotic (e.g., if they take doxycycline initially switch to amoxicillin (and vice versa)) for about 1-8 weeks (including 1, 2, 3, 4, 5, 6, 7 or 8 weeks) treatment period. After that they would be reassessed for response of symptoms and declining CCL19 level.

In a further aspect, the present disclosure provides compositions that can be employed in the disclosed methods. In certain embodiments, such compositions comprise a solid substrate and a plurality of binding agents immobilized on the substrate, wherein each of the binding agents is immobilized at a different, indexable, location on the substrate and the binding agents selectively bind to a plurality of biomarkers disclosed herein. In a specific embodiment, the locations are pre-determined. In other embodiments, kits are provided that comprise such compositions. In certain embodiments, the plurality of biomarkers includes one or more of the biomarkers described herein including CCL19.

In a related aspect, methods for treating PTLDS in a patient/subject can comprise the steps of (a) contacting a biological sample obtained from the subject with a composition disclosed herein comprising binding agents for a period of time sufficient to form binding agent-biomarker complexes; (b) detecting binding of the binding agents to a plurality of biomarkers, thereby determining the levels of biomarkers in the biological sample; and (c) comparing the determined levels to a control or reference sample. In another embodiment, the method can further comprise the step of (d) treating the patient with one or more treatment modalities appropriate for a subject having or likely to have (i.e., at risk of) PTLDS.

In specific embodiments, the assay performed on the biological sample can comprise contacting the biological sample with one or more capture agents (e.g., antibodies, lectins, peptides, aptamers, etc., combinations thereof) to form a biomarker:capture agent complex. The complexes can then be detected and/or quantified.

In one method, a first capture molecule or binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker is then used to detect binding of the biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, chips and microporous membranes constructed, for example, of nitrocellulose, nylon, polyvinylidene difluoride, polyester, cellulose acetate, mixed cellulose esters and polycarbonate. Suitable microporous membranes include, for example, those described in US Patent Application Publication no. US 2010/0093557 A1. Methods for the automation of immunoassays are well known in the art and include, for example, those described in U.S. Pat. Nos. 5,885,530, 4,981,785, 6,159,750 and 5,358,691.

The presence of several different biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in US Patent Application Publication nos. US2010/0093557A1 and US2010/0190656A1, the disclosures of which are hereby specifically incorporated by reference.

Multiplex arrays in several different formats based on the utilization of, for example, flow cytometry, chemiluminescence or electron-chemiluminesence technology, are well known in the art. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis. In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate. In specific embodiments, the cytokine biomarkers are detected using the Bio-Plex® Multiplex System (Bio-Rad Laboratories, Inc. (Hercules, Calif.)).

B. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

C. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In specific embodiments, the biomarkers of the present invention are detected using nanotechnology including, for example, a nanowire. See, e.g., U.S. Pat. No. 8,323,466 and U.S. Patent Application Publication No. 20120258445 (NanoIVD, Inc. (Los Angeles, Calif.)).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 00/56934; and PCT International Publication No. WO 03/048768.

III. Determination of a Patient's Lyme/PTLDS Status

The biomarkers of the present invention can be used in diagnostic tests to assess, determine, and/or qualify (used interchangeably herein) Lyme/PTLDS status in a patient and therefore, direct treatment of the patient. The biomarkers the cytokines described herein including CCL19. Based on this status, further procedures may be indicated, including additional diagnostic tests or therapeutic procedures or regimens.

These and other biomarkers are disclosed herein, and it is understood that when combinations, subsets, interactions, groups, etc., of these biomarkers are disclosed that while specific reference of each various individual and collective combinations and permutation of these compounds may not be explicitly disclosed, each is specifically contemplated and described herein. Thus, if a panel of biomarkers A, B, and C are disclosed as well as a class of biomarkers D, E, and F and an example of a combination panel A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of using the disclosed biomarkers. Thus, if there are a variety of additional steps that can be performed, it is understood that each of these additional steps can be performed with any specific embodiment or combination of embodiments of the disclosed methods.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different Lyme/PTLDS statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

In certain embodiments, the biomarkers are measured in a patient sample using the methods described herein and a Lyme/PTLDS status is calculated. In particular embodiments, the measurement(s) may then be compared with a relevant diagnostic amount(s), cut-off(s), or multivariate model scores that informs the Lyme/PTLDS status. The diagnostic amount(s) represents a measured amount of a biomarker(s) above which or below which a patient is classified as having a particular Lyme/PTLDS status. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with different Lyme/PTLDS statuses, and drawing the cut-off to suit the desired levels of specificity and sensitivity.

Furthermore, in certain embodiments, the values measured for markers of a biomarker panel are mathematically combined and the combined value is correlated to the underlying diagnostic question of Lyme/PTLDS status. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree- Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Serum Inflammatory Mediators as Markers of Human Lyme Disease Activity Chemokines and cytokines are key signaling molecules that orchestrate the trafficking of immune cells, direct them to sites of tissue injury and inflammation and modulate their states of activation and effector cell function. We have measured, using a multiplex-based approach, the levels of 58 immune mediators and 7 acute phase markers in sera derived from of a cohort of patients diagnosed with acute Lyme disease and matched controls. This analysis identified a cytokine signature associated with the early stages of infection and allowed us to identify two subsets (mediator-high and mediator-low) of acute Lyme patients with distinct cytokine signatures that also differed significantly ($p,0.0005$) in symptom presentation. In particular, the T cell chemokines CXCL9 (MIG), CXCL10 (IP-10) and CCL19 (MIP3B) were coordinately increased in the mediator-high group and levels of these chemokines could be associated with seroconversion status and elevated liver function tests ($p=0.027$ and $p=0.021$ respectively). There was also upregulation of acute phase proteins including CRP and serum amyloid A. Consistent with the role of CXCL9/CXCL10 in attracting immune cells to the site of infection, CXCR3+ CD4 T cells are reduced in the blood of early acute Lyme disease ($p=0.01$) and the decrease correlates with chemokine levels ($p=0.0375$). The levels of CXCL9/10 did not relate to the size or number of skin lesions but elevated levels of serum CXCL9/CXCL10 were associated with elevated liver enzymes levels. Collectively these results indicate that the levels of serum chemokines and the levels of expression of their respective chemokine receptors on T cell subsets may prove to be informative biomarkers for Lyme disease and related to specific disease manifestations.

Materials and Methods

Patient Cohort.

The serum and PBMC samples used have been generated as part of a prospective cohort study with age- and sex-matched controls enrolled from 2008-2013. This study included a well-defined cohort of patients with acute Lyme disease enrolled from a Lyme endemic area of the mid-Atlantic United States. Only patients with untreated, confirmed early Lyme disease manifesting an active EM skin lesion at the time of enrollment, as defined by CDC case criteria were eligible [6,11,14]. Patients with a history of prior Lyme disease or the presence of confounding preexisting medical conditions associated with prolonged fatigue, pain or neurocognitive symptoms were excluded [45]. Controls were non-hospitalized age- and sex-matched and had no prior history of Lyme disease or any exclusionary medical conditions including lack of inflammatory disorders. The enrolled Lyme disease patients were followed from the time of acute infection longitudinally for a period of 2 years for a total of 7 study visits. The matched controls were followed for 2 years across 4 study visits. At each study visit, extensive clinical data and biological specimens were collected (see below).

Clinical Data Assessment.

At the pre-treatment study visit, a standard Complete Blood Count (CBC) and Comprehensive Metabolic Panel (CMP) were drawn and performed at an internal laboratory. In addition to these clinical tests, an additional SST tube was drawn to be sent to an outside, commercial laboratory for Lyme serology testing. Serology results were determined following the CDC's two-tier testing algorithm measuring both IgM and IgG, with time of symptom onset being determined by a structured interview with the patient at the pre-treatment study visit [6,11,14]. For those patients who were negative according to the two-tier serology at the first study visit, a subsequent serology was drawn at the second study visit after antibiotic treatment and sent to the same commercial laboratory for testing.

At each study visit, patients were given a physical exam, a structured interview of twenty signs and symptoms of disease, and underwent a blood draw. At the first visit, a measurement of the EM was taken and recorded.

Cytokine/Chemokine Assays.

We performed multiplex analysis of 58 cytokines/ chemokines and 7 acute phase markers using the Bio-Plex™ bead array system as recommended by the manufacturer and using previously described optimized assay protocols [46-49]. Data processing was performed using Bio-Plex manager software version 4.4.1 and serum concentrations were interpolated from standard curves for each respective cytokine. This protocol and data generated were MAIME compliant and were deposited in the Gene Expression Omnibus Repository (accession number GSE55815).

Flow Cytometry.

Peripheral blood mononuclear cells (PBMCs) were isolated from fresh heparinized blood using Ficoll Hypaque. Monoclonal antibody reagents specific for CD3 (UCHT1), CD4 (RPA-T4), CD8 (SK1) and CXCR3 (IC6) were purchased from Becton Dickenson. PBMCs were first incubated with unlabeled human IgG to block nonspecific binding followed by incubation with fluorescent tagged monoclonal reagents. PBMCs were washed and polychromatic flow cytometry performed using a FACSAria instrument (Becton Dickinson, San Jose, Calif.). Lymphocytes were gated using forward and side scatter and the data analyzed using FlowJo software (Tree Star).

Statistical Analysis.

For descriptive analyses of the multiplex biomarker data as continuous variables, data was analyzed using the log of the "ratio to average". The log of the ratio to average was calculated by setting all values less than 1 pg/mL to 1 pg/mL, and then calculating the log base 2 of [(value)/(average value in the cohort)]. The "ratio to average" values were input into SAM (Significance Analysis of Microarrays Version 4.0) [50]. The SAM output was sorted based on false discovery rates (FDRs, represented by the q value) in order to identify mediators with the greatest differences in levels between patient subgroups. We used hierarchical clustering software Cluster 3.0 to arrange the SAM results according to similarities among mediator levels, with no markers weighted in FIG. 1A, and with weighting of CCL19 and Serum Amyloid A was used in the clustering for FIG. 1B. The clustered results were displayed using Java Treeview (Version 1.1.5r2).

Categorical variables were analyzed using Fisher's Exact or Chi-square statistics. A standard ANOVA or unpaired t-test was used on two or more group comparisons for continuous variables. Pearson correlations were used for linear comparisons. For longitudinal continuous variables, a repeated measures ANOVA was performed. All statistical calculations were performed with SPSS software (IBM Corporation v 21).

Ethics Statement.

All human subject studies in this manuscript were reviewed and approved by the Johns Hopkins School of Medicine Institutional Review Board (protocol NA 00011170). All subjects recruited in the study were adults and all were provided written informed consent.

Results

Identification of a Cytokine/Chemokine Signature Associated with Acute Lyme Disease. We have conducted a prospective cohort study of acute Lyme disease and post-treatment events (see Table 1). All patients enrolled in the study have untreated early Lyme disease that meets the Infectious Disease Society of America (IDSA) criteria for diagnosis [6,11,14]. Using samples collected from this cohort we employed a bead-based multiplex cytokine assay to measure the levels of 58 immune mediators and 7 acute phase proteins in the serum of patients with untreated early (acute) Lyme and matched controls. Displayed in FIG. 1A is a heat map of those mediators significantly elevated (q,0.1%) in early acute Lyme disease at the initial pre-treatment visit compared to controls. Most notable are elevated levels of several T cell chemokines (CCL19, CXCL9, CXCL10), acute phase inflammatory markers (CRP and serum amyloid A), several IL-1 cytokine family members (IL-lra, IL-18, IL-33), inflammatory cytokines TNF-α and IL-6 and the T cell cytokine IL-2. Collectively, these cytokines and chemokines generate a novel signature that clearly distinguishes acute Lyme patients from normal controls.

Figure 1B:
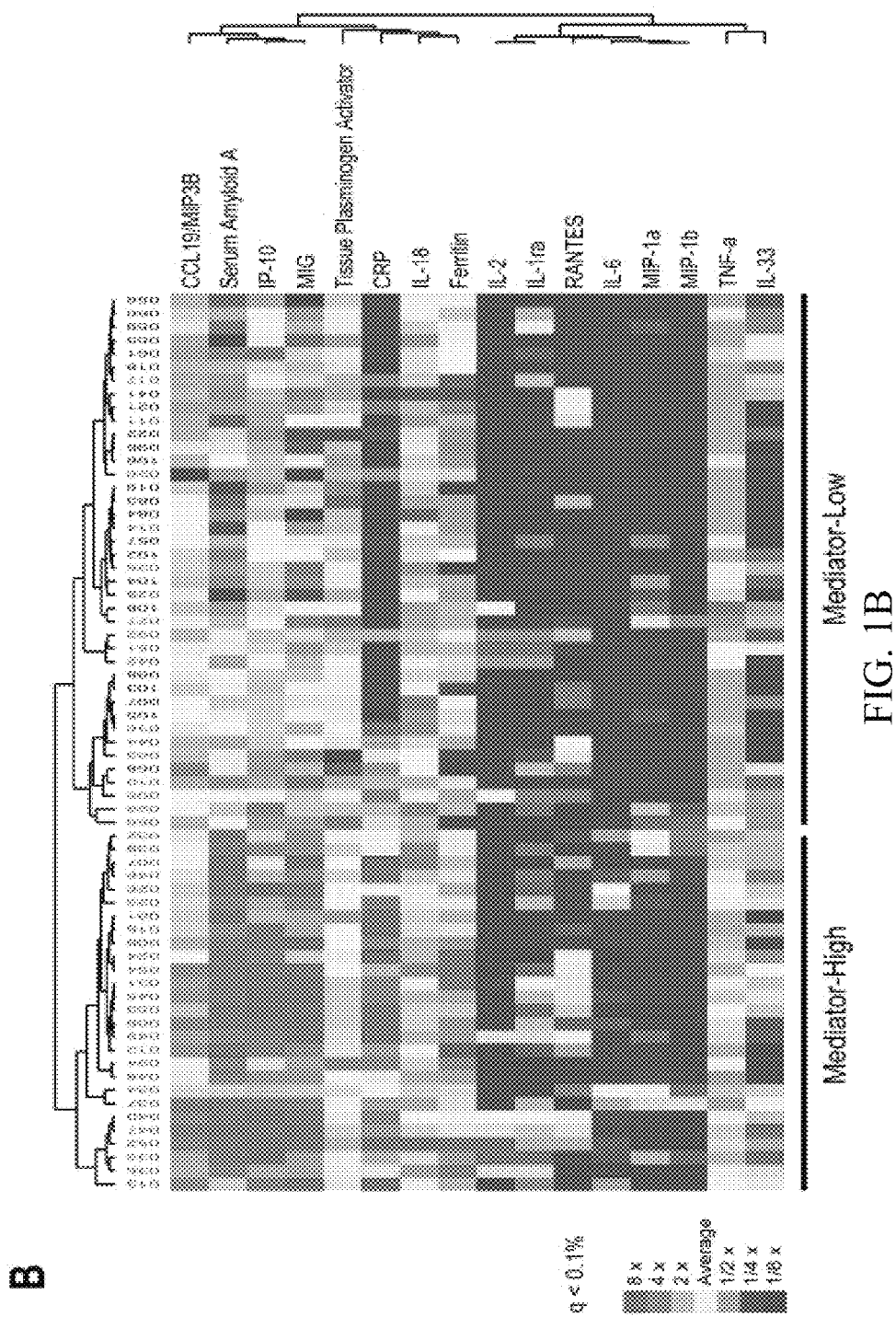

Displayed in FIG. 1B is an unsupervised hierarchical clustering of the serum mediator profiles of the same early acute Lyme disease at the initial pre-treatment visit and control patients. This analysis allows us to distinguish two patient clusters of acute Lyme disease patients. One group termed mediator-high, displayed elevated levels of the T cell chemokines and inflammatory markers during acute infection described above. A second group of Lyme disease patients (mediator-low) displayed mediator levels that result in their clustering among normal control samples. Since all patients met IDSA guidelines for acute Lyme disease, the mediator-low group represents a subset of Lyme patients that did not exhibit significant elevations in inflammatory mediators in blood.

Acute Lyme Disease Patient Defined Subgroups Have Distinct Clinical Features.

Based on immune mediator levels during acute infection, two subgroups of Lyme patients could be distinguished. Table 2 presents a comparison of these two groups for a range of clinical outcomes. No differences in demographics, duration of illness or the distribution of single versus multiple erythema migrans lesions were noted between the two groups. However, significant differences were noted in the number of symptoms (p,0.005), absolute lymphocyte levels (p=0.002), liver enzyme tests (p=0.027) and the presence of detectable anti-*Borrelia* antibodies (p=0.021). Lyme disease patients displaying high mediator levels at the initial pre-treatment visit (acute disease) had higher rates of seroconversion, but also had greater rates of lymphopenia and elevated liver enzyme.

T Cell Chemokine Levels are Selectively Elevated in the Acute Phase of Lyme Disease.

Figures 2A, 2B:
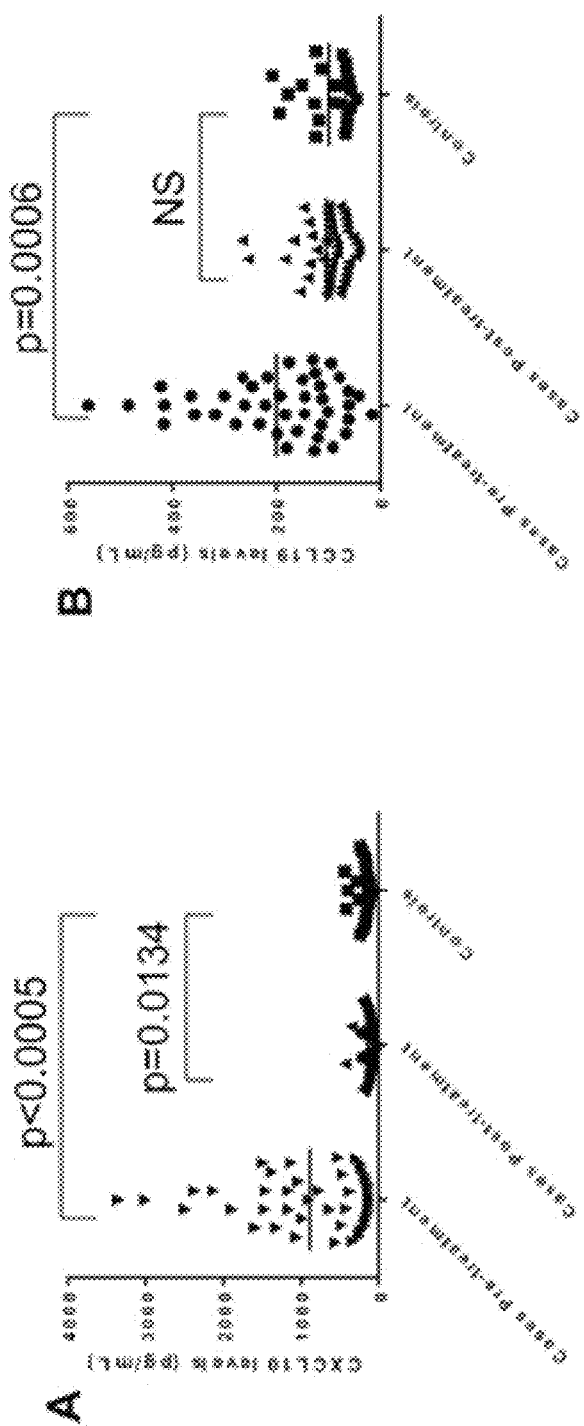
FIG. 2A-2D. Chemokine levels in Lyme disease before and after treatment. Displayed are the levels of the chemokines CXCL10 (FIG. 2A), CCL19 (FIG. 2B), CXCL9 (FIG. 2C) and CXCL8 (FIG. 2D) measured in the serum of Lyme patients (n=44) pre-treatment (acute disease) and post-treatment (4 weeks following diagnosis) as compared to healthy controls (n=23). Horizontal bars represent the medians for each sample group.
Figure 2D:
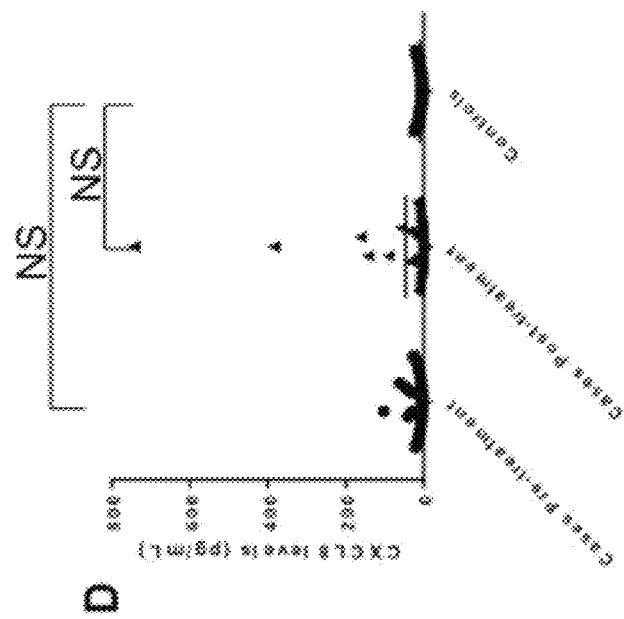
Figure 2C:
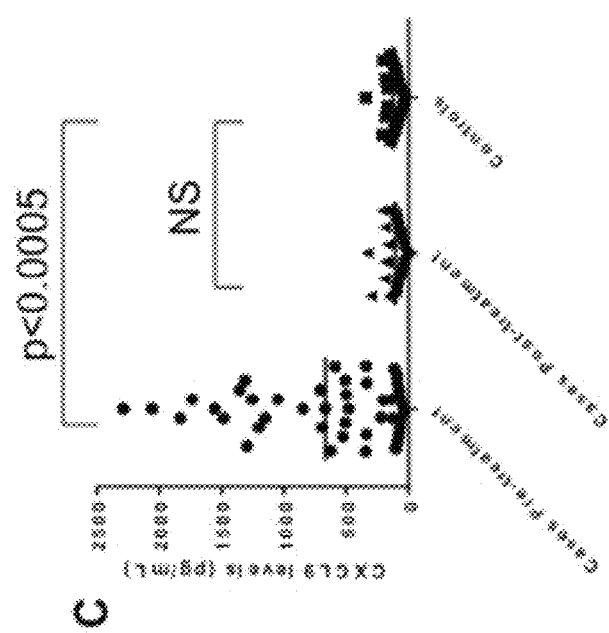

A striking feature of the cytokine/chemokine profile was the upregulation of T cell specific mediators. Displayed in FIGS. 4A-D are the measured levels of the chemokines CXCL9 (MIG), CXCL10 (IP-10), CCL19 and CXCL8 (IL-8) in sera obtained from patients at the time of their initial diagnosis of acute Lyme disease (pre-treatment), 4 weeks following diagnosis and treatment (post-treatment) and matched controls. The T cell chemoattractants CXCL9, CXCL10 and CCL19 were significantly elevated in serum during the acute infection but largely returned to normal levels following treatment, resolution of the erythema migrans and recovery. Levels of CXCL9, CXCL10 and CCL19 were completely concordant with one another (Table 3). In contrast, the neutrophil chemotactic factor CXCL8 was not elevated during acute infection or at other observed time points (FIG. 2D). Furthermore, the measured levels of CCL11 (eotaxin-1), CXCL1 (GROa), CCL2 (MCP-1), CCL7 (MCP-1), CCL3 (MIP-1a), CCL4 (MIP1b), CCL5 (RANTES) and CXCL12 (SDF-1a) were not significantly different as compared to the levels in matched controls (data not shown). Therefore in acute Lyme disease there appears to be a selective and coordinate elevation of T cell chemoattractants.

Innate Serum Inflammatory Markers Are Up-Regulated During the Acute Lyme Disease.

As revealed in the global serum profiling shown in FIG. 1, the cytokine IL-6 and the innate immune acute phase factors C-reactive protein (CRP) and serum amyloid A (SAA) are elevated during acute Lyme disease. A more detailed analysis of the levels over time is presented in FIG. 3. Increased levels of CRP (p=0.0091), SAA p,0.0005) and IL-6 (p=0.0282) were seen during the acute phase. CRP and SAA levels returned to normal control levels following treatment and remained so throughout the follow-up period. IL-6 levels remained elevated and only returned to normal levels months after infection and treatment. As is the case for the T cell chemokines, serum CRP and SAA significantly correlated with one another (Table 3, p=0.016). Surprisingly, IL-6, a known inducer of CRP and SAA did not correlate with these acute phase proteins (p=0.09 and 0.54 respectively, Table 3).

Chemokine and Inflammatory markers: correlation with Liver Function Abnormalities.

Figures 3A, 3B, 3C:
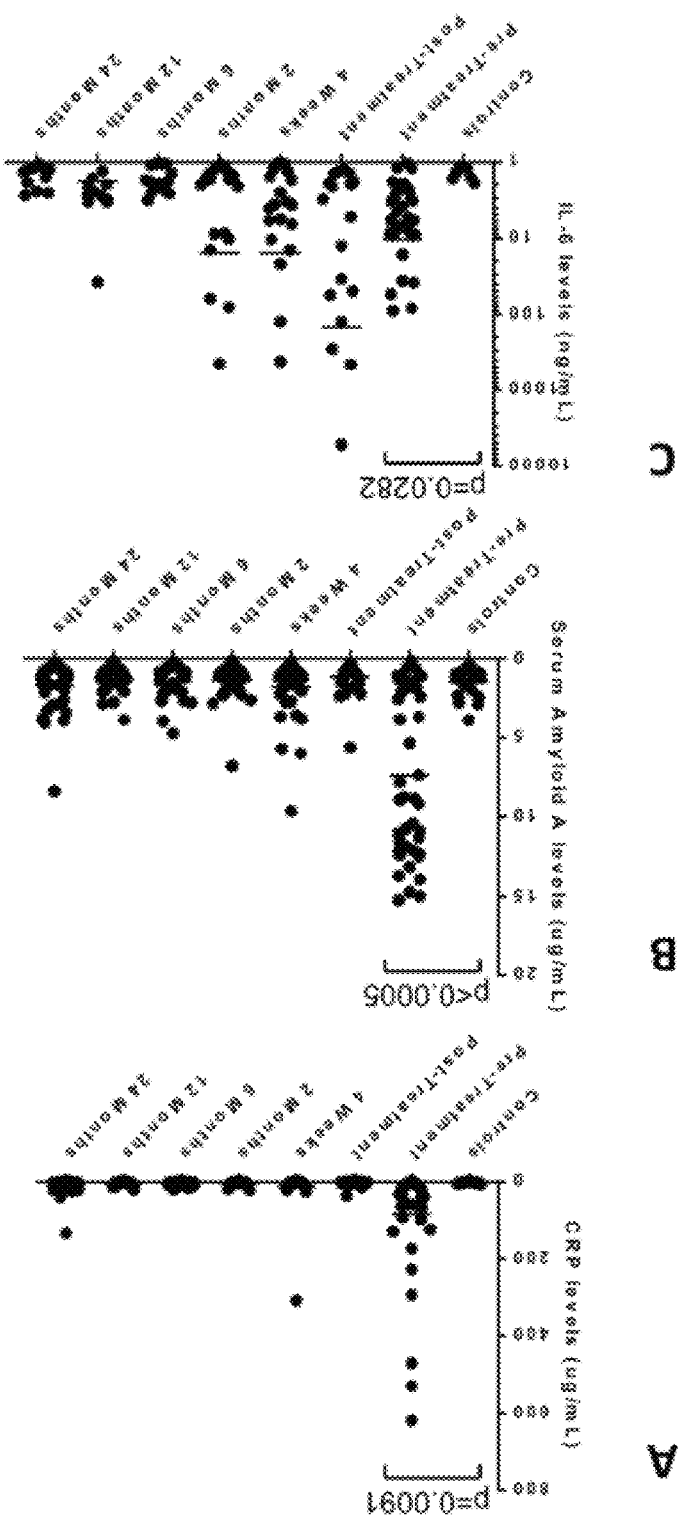
FIG. 3A-3C. Elevated Inflammatory Mediators in Lyme Disease. Serum levels of CRP (FIG. 3A), Serum Amyloid A (FIG. 3B) and IL-6 (FIG. 3C) were measured in healthy controls (n=23) and at various times during the course of diagnosis and treatment in Lyme patients (n=44). CRP, Serum Amyloid A and IL-6 levels are significantly elevated at diagnosis (pre-treatment). CRP and Serum Amyloid A levels return to control levels after treatment while IL-6 levels persist.
Figure 4A:
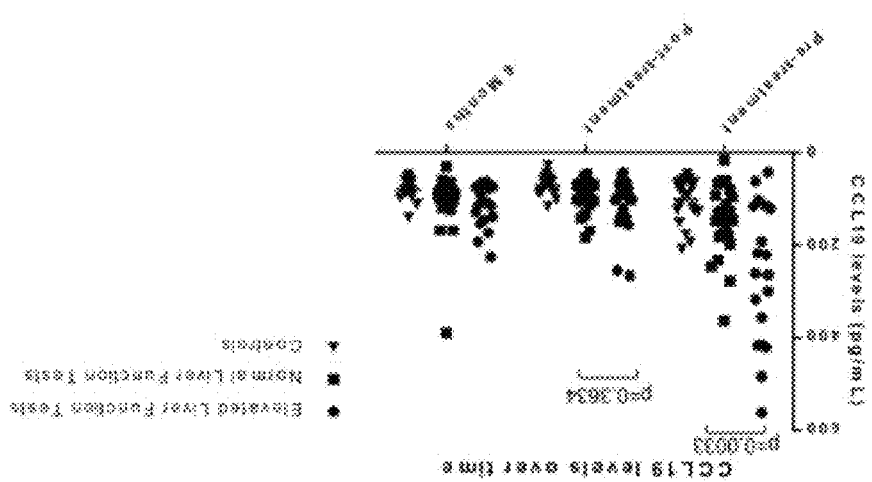
FIG. 4A-4C. Chemokine levels are associated with elevated liver function tests. Lyme patients were separated into two populations based on normal (n=24) vs. elevated liver enzyme tests (n=20) and the levels of CXCL10 (FIG. 4A), CXCL9 (FIG. 4B) and CXCL10 (FIG. 4C) compared at three visits (pre-treatment, post-treatment, and 6 months) relative to healthy controls (n=23). All three chemokines are significantly different between Lyme patients with high liver function tests and those with normal liver function tests at the pre-treatment visit. This difference was not observed at later time points.
Figure 4B:
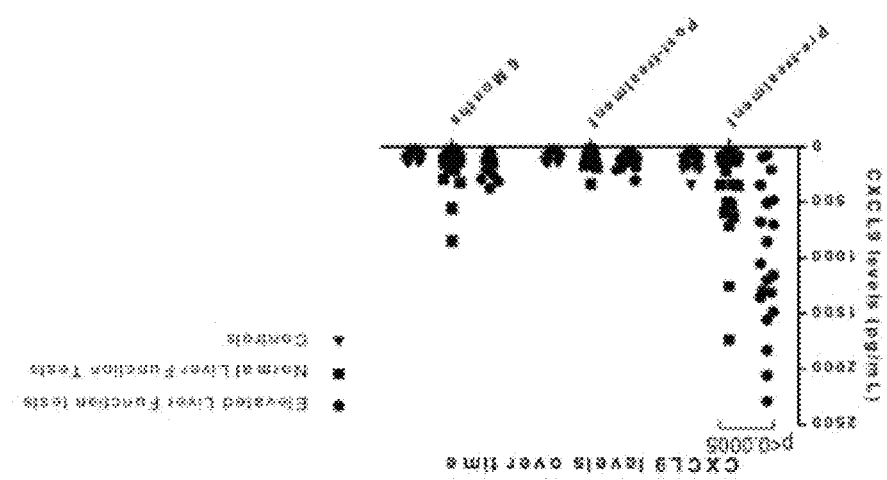
Figure 4C:
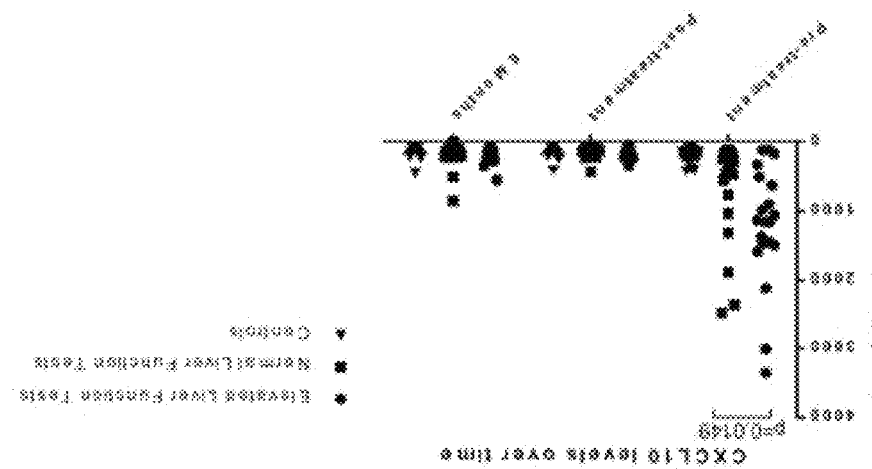

T cell chemokine levels in acute Lyme patient sera, while clearly elevated, did show heterogeneity with a subset displaying levels similar to controls (FIGS. 4A-C). A similar case can be made for the inflammatory biomarkers CRP and serum amyloid A (FIG. 3). This heterogeneity suggests that individual chemokine and/or inflammatory markers may correlate with clinical parameters.

The erythema migrans (EM) lesion is the primary site of inflammation in acute Lyme disease and it can vary in size as well as number. This lesion is characterized as the site of active bacterial growth and the accumulation of immune inflammatory cells that is dominated by T cells [9,15,16]. The chemokines CXCL9 and CXCL10 were present at high levels within the EM lesion likely produced by fibroblasts and endothelial cells in an interferon-c dependent manner [15-17]. Based on this we reasoned that the levels of CXCL9 and/or CXCL10 might correlate either with the size or degree of dissemination of the EM lesion. Within the Lyme cohort, a significant proportion of patients had disseminated lesions and the size of the lesions was varied (Table 1). Surprisingly, when we compared these variables with the levels of serum CXCL9 and CXCL10 there was no statistical association (data not shown).

Previous studies have also described changes in liver enzyme levels during acute Lyme disease [18,19]. This pattern is also observed in the current cohort of Lyme disease patients (Table 1). When we compared the levels of serum CXCL9/CXCL10 among the acute Lyme patients with high liver enzyme levels, there was a significant association of high CXCL9/CXCL10 and CCL19 levels with elevated liver enzymes in the acute phase of Lyme disease (FIG. 4).

Figure 5B:
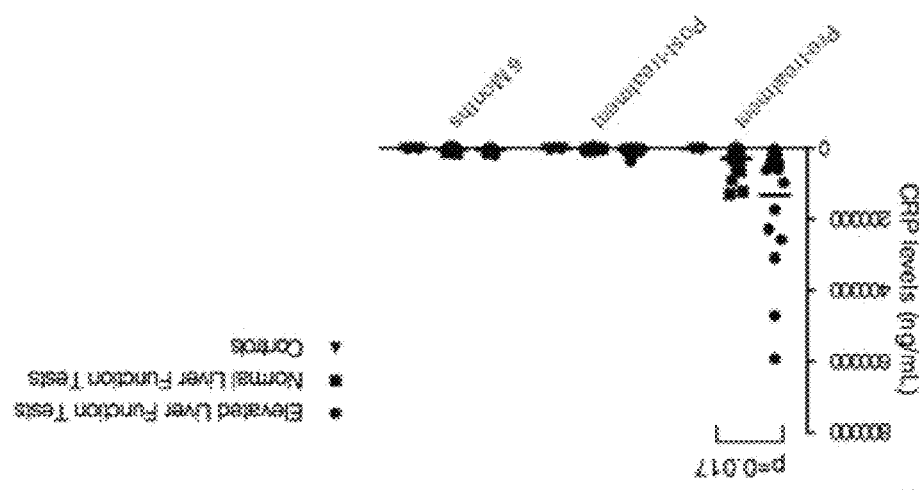
FIG. 5A-5B. Serum Amyloid A levels are associated with elevated liver function tests. Lyme patients were separated into two populations based on normal (n=24) vs. elevated liver enzyme tests (n=20) and the levels of Serum Amyloid A (FIG. 5A) and CRP (FIG. 5B) were compared at multiple time points relative to healthy controls (n=23). Serum amyloid A (p=0.036) and CRP (p=0.017) levels are significantly different between Lyme patients with high liver function tests at the pre-treatment visit. Both groups are significantly different from controls at (p<0.0005), but are not different from each other or controls, at both the Post-treatment and 6 Month follow-up visits. There is no significant difference in CRP levels between high and normal liver function groups, however both are significantly different from controls (p<0.0005).

The finding that liver enzymes and acute inflammatory markers were elevated in acute Lyme disease suggested that there these two markers may be related. As shown in FIG. 5, CRP and SSA but not IL-6 (data not shown) levels correlated with liver enzyme levels.

High T cell Chemokine Levels are Associated with Seroconversion.

In this patient cohort, 35.7% of Lyme patients failed to test positive either at diagnosis or through seroconversion following antibiotic treatment (Table 1). This is consistent with previous studies that demonstrated that a significant fraction of Lyme patients that exhibit EM along with other symptoms of infection do not seroconvert when assayed by the current two-tiered testing [11,12]. When we examined whether various elevated mediator levels could be correlated with seroconversion status, a significant association was observed with elevated CXCL9 and CXCL10 but not CCL19 levels (Table 4). When other clinical parameters such as duration of illness or size/dissemination of EM lesions (data not shown) were analyzed, there was no association with seroconversion status.

CXCR3 Expressing T cells are Decreased in Lyme Disease and Co-relate with CXCL9/CXCL10 Levels.

The chemokines CXCL9 and CXCL10 bind to a common receptor CXCR3 expressed largely on T cells [20]. We reasoned that high serum levels of these chemokines may drive T cells into inflamed tissues and as a result levels of CXCR3 expressing T cells may be altered during acute Lyme disease. Levels of CXCR3+CD4 T cells were determined by polychromatic flow cytometry (FIG. 6A), and found to be significantly lower in the blood of patients with acute Lyme disease versus controls (FIG. 6B). In addition, serum levels of CXCL10 (FIG. 6C) and CXCL9 (data not shown) were inversely related to the frequency of CXCR3+CD4+ T cells in the peripheral circulation.

DISCUSSION

Utilizing a multiplex-based assay for 65 immune and inflammatory mediators, a clear coordinated cytokine/chemokine signature was identified that distinguished patients with acute Lyme disease from normal non-inflammatory controls. Furthermore, variation in this signature allowed us to define at least two groups of Lyme disease patients with clear differences in the levels of key mediators. Interestingly, these subgroups of Lyme patients had distinct disease characteristics including number of symptoms, lymphopenia, elevated liver function and rate of seroconversion. At this time we cannot determine if this signature is acute Lyme specific or more reflects a general inflammatory signature. However, a similar analysis of serum from patients with Rheumatoid Arthritis identified a distinct cytokine signature that included Eotaxin, Il-12p40 and Rantes, mediators that were not elevated in our Lyme disease cohort (46-49).

CXCL9, CXCL10 and CCL19 are three prominent chemokines that were elevated in our cohort of acute Lyme disease patients. All three mediators are coordinately elevated and return to baseline control levels following treatment and resolution of the EM. Previous work has shown elevated levels of CXCL9 and CXCL10 within the EM skin lesion and in the sera of patients with early acute Lyme disease, as well as in the synovial fluid and tissue of patients with Lyme arthritis [16,17,21-23]. Similar to our observations, the levels of serum CXCL9 and CXCL10 can vary among acute Lyme disease patients and levels correlate with severity of disease [23]. Elevated levels of CXCL9 and CXCL10 are found in a number of Th1 driven immune inflammatory settings including autoimmune disorders and viral, bacterial and protozoan infections [20,24,25].

The chemokines CXCL9 and CXCL10 are produced by macrophages and non-immune cells within inflamed tissues in an interferon-dependent manner. These chemokines bind to the chemokine receptor CXCR3 expressed largely on antigen activated T cells [20]. The primary site of inflammation and bacterial replication in early acute Lyme disease is thought to be the skin EM lesion. Previous work has shown that this site expresses high levels of CXCL9 and CXCL10 and CXCR3+ T cells [15,17]. Our finding that high levels of serum CXCL9 and CXCL10 levels are associated with lymphopenia and correlate with lower levels of blood CXCR3+ T cells supports a model where infection-induced tissue inflammation and chemokine production drives the recruitment of activated effector T cells from the blood into the site of infection. Therefore it was surprising when we observed no correlation of CXCL9 or CXCL10 levels with the size or extent of the EM. Interestingly, high levels of CXCL9 and CXCL10 were closely related with the extent of liver involvement as measured by blood liver enzyme levels. In mouse models, the liver is a well-defined site for *B.*

*burgdorferi* dissemination [26]. Also, liver function can vary among acute Lyme patients [18,27,28]. These observations suggest that *B. burgdorferi* induced liver involvement can, in part, be driving the serum levels of CXCL9 and CXCL10. Consistent with this is the finding that CXCL9 and CXCL10 recruits T cells in chronic liver diseases and that CXCR3+ effector T cells accumulate in the liver of *B. burgdorferi* infected mice [26,29]. Interestingly, CXCL10 levels correlate with severe liver damage levels in hepatitis-C infected patients [30,31]. Whether this is the case for Lyme disease requires further study.

To our knowledge this is the first observation that the serum levels of the chemokine CCL19 is elevated in acute Lyme disease. Previous work has shown an increase in the cerebrospinal fluid (CSF) in subjects with Lyme neuroborreliosis where CXCL19, along with CXCL13, is proposed to play a role in B cell recruitment [32]. CCL19 is a ligand for CCR7 and plays an important role in the homing of B and T lymphocytes and dendritic cells to the lymph node to facilitate cellular interactions essential for the generation of an effective immune response [33,34]. The coordinated elevation of CXCL9, CXCL10 and CCL19 in acute Lyme disease is consistent with an ongoing host immune response in the draining lymph nodes accompanied by the generation of *Borrelia*-reactive effector T cells and their migration into the site of infection. These conditions would be predicted favor the generation of an effective antibody response and, indeed seroconversion is significantly associated with elevated levels of CXCL9 and CXCL10.

The detection of a subgroup of acute Lyme patients that display low levels of immune mediators in the blood (mediator-low) could represent a set of immunologically hyporesponsive individuals or patients that have immunologically cleared the infection for which inflammation has subsided. The finding that both mediator groups have similar duration of illness and identical erythema migrans presentation together with the observation that the mediator-low group is also enriched for seronegative patients argues against but does not fully exclude the latter possibility. Of note the mediator low group is heterogeneous in how Lyme patients cluster with controls suggesting that indeed there may be multiple mechanisms underlying the mediator low group. The failure to seroconvert is a well-known feature of antibiotic treated early Lyme disease but the underlying cause is not understood [11,12]. It is also unlikely that the non-seroconverting Lyme disease patients were missed due to a delayed response because in the study design patients with a seronegative test result at diagnosis were re-tested following treatment and remained negative. This argues that the mediator low group represents a subgroup of Lyme patients that develop a diminished immune response that leads, in some cases, to poor antibody production.

In a well-developed inbred mouse model, infection with *B. burgdorferi* led to disrupted germinal center formation, delays in the generation of long lived plasma cells and a weak, largely IgM antibody responses [35]. It was proposed that this outcome may be part of a *B. burgdorferi* evasion strategy to delay or avoid clearance. Although this was not tested in the above model, it is possible that *B. burgdorferi* strains may vary in evasive capabilities and be capable of stimulating a range of antibody responses. It is reasonable to speculate that the seronegative subjects within the mediator-low group may have been infected with a highly evasive *B. burgdorferi* strain. This is supported by the finding that chemokine (CXCL9 and CXCL10) and cytokine levels can vary in Lyme disease patients depending on the genotype of the infecting *B. burgdorferi* [21]. Alternatively, and perhaps more likely, the host genetic environment may play a role as TLR-1 polymorphisms are linked to chemokine (CXCL9 and CXCL10) and cytokine levels [23].

Figure 5A:
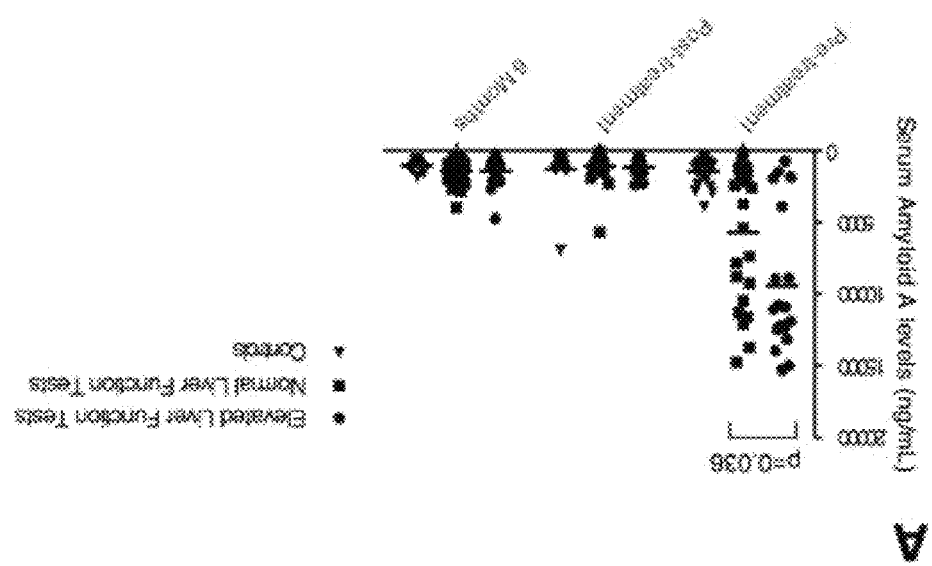

CRP is a short pentraxin produced by the liver and functions as a fluid phase pattern recognition molecule [36]. SAA is a serum lipoprotein that can recognize bacteria by interacting with outer membrane proteins [37,38]. CRP and SAA are synthesized by hepatocytes and IL-6 has been identified as a strong stimulator of CRP and SAA production [36,37,39,40]. Infection with *B. burgdorferi* clearly stimulates the coordinated production CRP and SAA along with IL-6 during the acute stage of Lyme disease. Therefore it was surprising that the levels of serum CRP and SAA reactants correlate poorly with serum IL-6. This implies that IL-6 independent events may be driving production. Alternatively, the increases in CRP, and SAA could reflect the localized production of IL-6 in the liver, possibly as a site of infection, inflammation and/or tissue injury in the early acute Lyme phase [41]. This latter scenario is supported by the association of SAA and CRP levels with elevated serum liver enzymes (FIG. 5A).

The finding that IL-6 levels remain elevated in some patients through the latter stages of Lyme disease was surprising. This suggests that in a subset of patient diagnosed with acute Lyme individuals, following treatment, there is an ongoing inflammatory event driving IL-6 production. The liver is likely not the site of inflammation as CRP and SAA levels return to normal post-treatment. One possibility is that there is residual antigen or infection in some treated Lyme disease patients but this is a controversial area. Evidence from mouse and primate models supports either the persistence of live bacteria or antigens after antibiotic treatment following Lyme borreliosis [42-44]. Convincing validation of these studies in the human setting is not available. Nevertheless, our observations suggest that there is an ongoing process that is selectively driving IL-6 production, the mechanistic basis of this awaits further study. Future studies need to examine if there is any relationship of persistently elevated IL-6 levels or other inflammatory markers with long-term outcomes such as PTLDS.

The analysis of chemokine and cytokine levels in the serum of Lyme disease patients has allowed us to define at least two subsets of Lyme patients which have distinct disease phenotypes differing in number of symptoms, extent of liver involvement, lymphocyte levels and seroconversion status. It is possible that the inflammatory mediator profiles identified may prove valuable as biomarkers of Lyme disease activity. Moreover, these chemokines likely identify immune pathways that are involved in the resolution of Lyme disease and as such may be potential therapeutic targets.

TABLE 1

Cohort Characteristics.

| | | Cases (n = 44) | Controls |
|---|---|---|---|
| Demographics | | | |
| Sex | Male | 56.8% | 43.5% |
| | Female | 43.2% | 56.5% |
| Age | | 49.41 ± 16.241 (20-75) | 56.22 ± 12.645 (22-73) |
| Race | White | 95.5% | 95.7% |
| | Black | 2.3% | 2.3% |
| | Other | 2.3% | 2.3% |
| Education* | | 15.91 ± 2.675 (11-21) | 17.74 ± 2.435 (12-21) |
| Clinical Characteristics** | | | |
| Serogroup | Non-converter | 35.7% | |
| | Converter | 26.2% | |

TABLE 1-continued

Cohort Characteristics.

|  |  | Cases (n = 44) | Controls |
|---|---|---|---|
|  | Positive at diagnosis | 38.1% |  |
| Lesion type | Single | 65.9% |  |
|  | Disseminated | 34.1% |  |
| Area (cm$^2$) of primary lesion |  | 96.73 ± 98.96 (11.78-466.53) |  |
| Liver enzyme tests | Normal | 56.8% |  |
|  | Elevated | 43.2% |  |
| Lymphopenia status | Normal | 59.1% |  |
|  | Lymphopenic | 40.9% |  |

*= Statistically different between cases and controls (p = 0.008), but not clinically significant
**= Early Lyme disease cohort only; these characteristics do not apply to control participants.
doi:10.1371/journal.pone.0093243.t001

TABLE 2

Acute Lyme Disease patient subsets defined by circulating mediators versus clinical phenotypes.

|  |  | Acute Lyme Mediator High n = 27 mean (SD) | Acute Lyme Mediator Low n = 17 mean (SD) | Significance |
|---|---|---|---|---|
| Sex | Female | 44% | 41.2% | NS |
|  | Male | 55.6% | 58.8% |  |
| Lymphocyte number |  | 1.07 (0.41) × 10$^3$ μl | 1.58 (0.63) × 10$^3$ μl | p = 0.002 |
| Lymphopenia status | Lymphopenic | 70.4% | 29.4% | p = 0.013 |
|  | Non-lymphopenic | 29.6% | 70.6% |  |
| Liver Enzyme Group[a] | High liver enzyme | 61.5% | 23.5% | p = 0.027 |
|  | Normal liver enzyme | 38.5% | 76.5% |  |
| Serology[b] | Seropositive | 77.8% | 40% | p = 0.021 |
|  | Seronegative | 22.2% | 60% |  |
| EM Presentation | Single Lesion | 66.7% | 64.7% | NS |
|  | Disseminated Lesions | 33.3% | 35.7% |  |
| Number Symptoms Pre-treatment |  | 8.45 (3.45) | 4.15 (1.95) | p < 0.0005 |
| Illness Duration (days) |  | 6.89 (4.48) | 12.59 (11.65) | NS |

Table 2 shows group differences based on the heat map generated using SAM (see FIG. 1). No demographic differences between groups were seen. Categorical variables were compared using Fisher's Exact tests, while continuous variables were compared using impaired t-tests. Lymphocyte values given are mean (standard deviation), while other values given are a percentage of the respective subset. Number of symptoms pre-treatment is defined as the number of symptoms reported by the patient during structured interview by the principle investigator (JNA) or study staff (LAC). Illness duration is defined as the period of time between first sign or symptom of disease and presentation for treatment and enrollment in the study.
[a]Acute Lyme Mediator High n = 26; Acute Lyme Mediator Low n = 17;
[b]Acute Lyme Mediator High n = 27; Acute Lyme Mediator Low n = 15.
doi:10.1371/journal.pone.0093243.t002

TABLE 3

Correlation Analysis of Key Mediators.

| Mediators | R value | Significance |
|---|---|---|
| CXCL9 vs. CXCL10 | 0.690 | p < 0.0005 |
| CCL19 vs. CXCL10 | 0.629 | P < 0.0005 |
| CCL19 vs. CXCL9 | 0.725 | P < 0.0005 |
| CRP vs. SAA | 0.373 | 0.016 |

TABLE 3-continued

Correlation Analysis of Key Mediators.

| Mediators | R value | Significance |
|---|---|---|
| IL-6 vs. CRP | 0.268 | NS |
| IL-6 vs. SAA | 0.094 | NS |

Table 3 shows the relationship between acute, pre-treatment levels of key immune mediators of early Lyme disease as discussed in this paper. Pearson correlations were used for all analyses. A significant correlation can be seen between CXCL10, CXCL9 and CCL19. CRP shows a significant positive correlation with Serum Amyloyd A (SAA). IL-6 does not correlate with either CRP or SAA.
doi:10.1371/journal.pone.0093243.t003

TABLE 4

Serostatus versus T Cell Chemokine Levels.

|  | Serology Negative | Serology Positive | Significance |
|---|---|---|---|
| CXCL10 < 800 pg/mL | 13 | 10 | p = 0.003 |
| CXCL10 ≥ 800 pg/mL | 2 | 17 |  |
| CXCL9 < 350 pg/mL | 11 | 7 | p = 0.004 |
| CXCL9 ≥ 350 pg/mL | 4 | 20 |  |
| CCL19 < 200 pg/mL | 11 | 15 | NS |
| CCL19 ≥ 200 pg/mL | 4 | 12 |  |

Cutoffs in early Lyme disease cases were created for CXCL10, CXCL9, and CCL19 based on being higher or lower than controls. The columns show differences between those who are sero-positive at either time of diagnosis or immediately following treatment and those who are negative at both time points for these three biomarkers. CXCL10 and CXCL9 show differences in the association between those who are sero-positive and sero-negative (p = 0.003 and p = 0.004 respectively). There is no statistical difference in the association between serogroups for CCL19.
doi:10.1371/journal.pone.0093243.t003

REFERENCES 1. (2013) Notice to readers: final 2012 reports of nationally notifiable infectious diseases. MMWR Morb Mortal Wkly Rep 62: 669-682.
2. (2007) Lyme disease—United States, 2003-2005. MMWR Morb Mortal Wkly Rep 56: 573-576.
3. (2000) Healthy People 2010: Understanding and Improving health. In: USDHHS, editor. 2nd ed: U.S. Govenrment Printing Office.
4. Coyle B S, Strickland G T, Liang Y Y, Pena C, McCarter R, et al. (1996) The public health impact of Lyme disease in Maryland. J Infect Dis 173: 1260-1262.
5. Campbell G L, Fritz C L, Fish D, Nowakowski J, Nadelman R B, et al. (1998) Estimation of the incidence of Lyme disease. Am J Epidemiol 148: 1018-1026.
6. Wormser G P, Dattwyler R J, Shapiro E D, Halperin J J, Steere A C, et al. (2006) The clinical assessment, treatment, and prevention of lyme disease, human granulocytic anaplasmosis, and babesiosis: clinical practice guidelines by the Infectious Diseases Society of America. Clin Infect Dis 43: 1089-1134.
7. Steere A C (2001) Lyme disease. N Engl J Med 345: 115-125.
8. Steere A C, Sikand V K (2003) The presenting manifestations of Lyme disease and the outcomes of treatment. N Engl J Med 348: 2472-2474.
9. Dandache P, Nadelman R B (2008) Erythema migrans. Infect Dis Clin North Am 22: 235-260, vi.
10. Duray P H (1989) Histopathology of clinical phases of human Lyme disease. Rheum Dis Clin North Am 15: 691-710.
11. Wormser G P (2006) Clinical practice. Early Lyme disease. N Engl J Med 354: 2794-2801.
12. Aucott J, Morrison C, Munoz B, Rowe P C, Schwarzwalder A, et al. (2009) Diagnostic challenges of early Lyme disease: lessons from a community case series. BMC Infect Dis 9: 79.

13. Steere A C, Glickstein L (2004) Elucidation of Lyme arthritis. Nat Rev Immunol 4: 143-152.
14. (1997) Case Definitions for Infectious Conditions Under Public Health Surveillance. Morb Mortal Wkly Rep 46: 1-55.
15. Salazar J C, Pope C D, Sellati T J, Feder H M Jr., Kiely T G, et al. (2003) Coevolution of markers of innate and adaptive immunity in skin and peripheral blood of patients with erythema migrans. J Immunol 171: 2660-2670.
16. Mullegger R R, Means T K, Shin J J, Lee M, Jones K L, et al. (2007) Chemokine signatures in the skin disorders of Lyme borreliosis in Europe: predominance of CXCL9 and CXCL10 in erythema migrans and acrodermatitis and CXCL13 in lymphocytoma. Infect Immun 75: 4621-4628.
17. Jones K L, Muellegger R R, Means T K, Lee M, Glickstein L J, et al. (2008) Higher mRNA levels of chemokines and cytokines associated with macrophage activation in erythema migrans skin lesions in patients from the United States than in patients from Austria with Lyme borreliosis. Clin Infect Dis 46: 85-92.
18. Horowitz H W, Dworkin B, Forseter G, Nadelman R B, Connolly C, et al. (1996) Liver function in early Lyme disease. Hepatology 23: 1412-1417.
19. Kazakoff M A, Sinusas K, Macchia C (1993) Liver function test abnormalities in early Lyme disease. Arch Fam Med 2: 409-413.
20. Groom J R, Luster A D (2011) CXCR3 ligands: redundant, collaborative and antagonistic functions. Immunol Cell Biol 89: 207-215.
21. Strle K, Jones K L, Drouin E E, Li X, Steere A C (2011) *Borrelia burgdorferi* RST1 (OspC type A) genotype is associated with greater inflammation and more severe Lyme disease. Am J Pathol 178: 2726-2739.
22. Shin J J, Glickstein L J, Steere A C (2007) High levels of inflammatory chemokines and cytokines in joint fluid and synovial tissue throughout the course of antibiotic-refractory lyme arthritis. Arthritis Rheum 56: 1325-1335.
23. Strle K, Shin J J, Glickstein L J, Steere A C (2012) Association of a Toll-like receptor 1 polymorphism with heightened Th1 inflammatory responses and antibiotic-refractory Lyme arthritis. Arthritis Rheum 64: 1497-1507.
24. Lee E Y, Lee Z H, Song Y W (2009) CXCL10 and autoimmune diseases. Autoimmun Rev 8: 379-383.
25. Liu M, Guo S, Hibbert J M, Jain V, Singh N, et al. (2011) CXCL10/IP-10 in infectious diseases pathogenesis and potential therapeutic implications. Cytokine Growth Factor Rev 22: 121-130.
26. Lee W Y, Moriarty T J, Wong C H, Zhou H, Strieter R M, et al. (2010) An intravascular immune response to *Borrelia burgdorferi* involves Kupffer cells and iNKT cells. Nat Immunol 11: 295-302.
27. Zanchi A C, Gingold A R, Theise N D, Min A D (2007) Necrotizing granulomatous hepatitis as an unusual manifestation of Lyme disease. Dig Dis Sci 52: 2629-2632.
28. Zaidi S A, Singer C (2002) Gastrointestinal and hepatic manifestations of tickborne diseases in the United States. Clin Infect Dis 34: 1206-1212.
29. Borchers A T, Shimoda S, Bowlus C, Keen C L, Gershwin M E (2009) Lymphocyte recruitment and homing to the liver in primary biliary cirrhosis and primary sclerosing cholangitis. Semin Immunopathol 31: 309-322.
30. Roe B, Coughlan S, Hassan J, Grogan A, Farrell G, et al. (2007) Elevated serum levels of interferon-gamma-inducible protein-10 in patients coinfected with hepatitis C virus and HIV. J Infect Dis 196: 1053-1057. Bauer J W, Baechler E C, Petri M, Batliwalla F M, Crawford D, Ortmann W A, Espe K J, Li W, Patel D D, Gregersen P K, Behrens T W: Elevated serum levels of interferon-regulated chemokines are biomarkers for active human systemic lupus erythematosus. PLoS Med 2006:e491.
31. Lagging M, Romero A I, Westin J, Norkrans G, Dhillon A P, et al. (2006) IP-10 predicts viral response and therapeutic outcome in difficult-to-treat patients with HCV genotype 1 infection. Hepatology 44: 1617-1625.
32. Rupprecht T A, Plate A, Adam M, Wick M, Kastenbauer S, et al. (2009) The chemokine CXCL13 is a key regulator of B cell recruitment to the cerebrospinal fluid in acute Lyme neuroborreliosis. J Neuroinflammation 6: 42.
33. Forster R, Davalos-Misslitz A C, Rot A (2008) CCR7 and its ligands: balancing immunity and tolerance. Nat Rev Immunol 8: 362-371.
34. Moschovakis G L, Forster R (2012) Multifaceted activities of CCR7 regulate Tcell homeostasis in health and disease. Eur J Immunol 42: 1949-1955.
35. Hastey C J, Elsner R A, Barthold S W, Baumgarth N (2012) Delays and diversions mark the development of B cell responses to *Borrelia burgdorferi* infection. J Immunol 188: 5612-5622.
36. Bottazzi B, Doni A, Garlanda C, Mantovani A (2010) An integrated view of humoral innate immunity: pentraxins as a paradigm. Annu Rev Immunol 28: 157-183.
37. Uhlar C M, Whitehead A S (1999) Serum amyloid A, the major vertebrate acutephase reactant. Eur J Biochem 265: 501-523.
38. Shah C, Hari-Dass R, Raynes J G (2006) Serum amyloid A is an innate immune opsonin for Gram-negative bacteria. Blood 108: 1751-1757.
39. Fujita T (2002) Evolution of the lectin-complement pathway and its role in innate immunity. Nat Rev Immunol 2: 346-353.
40. Bode J G, Albrecht U, Haussinger D, Heinrich P C, Schaper F (2012) Hepatic acute phase proteins—regulation by IL-6- and IL-1-type cytokines involving STAT3 and its crosstalk with N F-kappaB-dependent signaling. Eur J Cell Biol 91: 496-505.
41. Manfredi A A, Rovere-Querini P, Bottazzi B, Garlanda C, Mantovani A (2008) Pentraxins, humoral innate immunity and tissue injury. Curr Opin Immunol 20: 538-544.
42. Embers M E, Barthold S W, Borda J T, Bowers L, Doyle L, et al. (2012) Persistence of *Borrelia burgdorferi* in rhesus macaques following antibiotic treatment of disseminated infection. PLoS ONE 7: e29914.
43. Hodzic E, Feng S, Holden K, Freet K J, Barthold S W (2008) Persistence of *Borrelia burgdorferi* following antibiotic treatment in mice. Antimicrob Agents Chemother 52: 1728-1736.
44. Bockenstedt L K, Gonzalez D G, Haberman A M, Belperron A A (2012) Spirochete antigens persist near cartilage after murine Lyme borreliosis therapy. J Clin Invest 122: 2652-2660.
45. Wormser G P, Nadelman R B, Dattwyler R J, Dennis D T, Shapiro E D, et al. (2000) Practice guidelines for the treatment of Lyme disease. The Infectious Diseases Society of America. Clin Infect Dis 31 Suppl 1: 1-14.
46. Deane K D, O'Donnell C I, Hueber W, Majka D S, Lazar A A, et al. (2010) The number of elevated cytokines and chemokines in preclinical seropositive rheumatoid arthritis predicts time to diagnosis in an age-dependent manner. Arthritis Rheum 62: 3161-3172.
47. Lindstrom T M, Robinson W H (2010) Biomarkers for rheumatoid arthritis: making it personal. Scand J Clin Lab Invest Suppl 242: 79-84.

48. Chandra P E, Sokolove J, Hipp B G, Lindstrom T M, Elder J T, et al. (2011) Novel multiplex technology for diagnostic characterization of rheumatoid arthritis. Arthritis Res Ther 13: R102.
49. Hughes-Austin J M, Deane K D, Derber L A, Kolfenbach J R, Zerbe G O, et al. (2013) Multiple cytokines and chemokines are associated with rheumatoid arthritis-related autoimmunity in first-degree relatives without rheumatoid arthritis: Studies of the Aetiology of Rheumatoid Arthritis (SERA). Ann Rheum Dis 72: 901-907.
50. Tusher V G, Tibshirani R, Chu G (2001) Significance analysis of microarrays applied to the ionizing radiation response. Proc Natl Acad Sci USA 98: 5116-5121.

Example 2: CCL19 as a Chemokine Risk Factor for Post-Treatment Lyme Disease

Syndrome: A Prospective Clinical Cohort Study

Objectives:
Lyme disease (LD) is the most common vector-borne disease in the northern hemisphere. Approximately 10% of optimally treated patients develop persistent symptoms of unknown pathophysiology lasting six months or longer that negatively affect life functioning, known as post-treatment Lyme disease syndrome (PTLDS). The objective of this study was to investigate the association between clinical symptoms and a panel of immune mediators during and following treatment of early Lyme disease.

Methods:
Seventy-six patients with the erythema migrans rash were treated and followed at 5 time points over 1 year. At each visit, patients underwent a clinical evaluation, completed standardized surveys, and serum samples were drawn for measurement of 65 acute phase cytokines and chemokines. Patient values were compared across three clinical outcome groups and compared to control sample values.

Results:
Elevated levels of the T-cell chemokine CCL19 were associated with functionally significant, persistent symptoms at six and/or twelve months after diagnosis and treatment. A CCL19 cutoff of >115 pg/mL at one month post-treatment generated a sensitivity and specificity over 80%, and a relative risk of 13.25 for identifying those who would develop PTLDS at a later visit.

Conclusions:
The origin of persistently elevated CCL19 levels among PTLDS patients is unknown; however, we speculate that it may reflect an ongoing, immune-driven reaction at sites distal to secondary lymphoid tissue. The ability to identify a potential immunologic risk factor for PTLDS provides the opportunity to better understand the pathophysiology of PTLDS and to develop early interventions.

Materials and Methods

Patient Description.
Seventy-six patients with EM of greater than 5 cm were enrolled in a one-year prospective cohort study. Patients with a previous history of Lyme disease, or preexisting, confounding medical conditions associated with prolonged fatigue, pain, or neurocognitive symptoms were excluded. Cases were enrolled at time of acute infection, treated with three weeks of oral doxycycline, and seen regularly over the course of one year, for a total of six study visits (pre-treatment baseline, three weeks later following treatment, one month post-treatment, three months post-treatment, six months post-treatment, and one year post-treatment). Extensive clinical and biological specimen data were collected at each study visit. Twenty-six healthy, seronegative controls with no clinical history of Lyme disease were also enrolled. To control for random variability within the control group, samples were taken at two study visits 6 months apart and an average generated for each control participant. This study was approved by the Johns Hopkins Medicine Institutional Review Board. Informed consent was obtained from all patients prior to enrollment.

An operationalized definition of PTLDS that includes both persistent symptoms and functional impact [23] was retrospectively applied to all patients at the six month and one year follow-up visits. Briefly, this definition requires the presence of at least one of: new-onset or worsening fatigue, new-onset musculoskeletal pain in at least three areas of the body, and cognitive complaints of difficulty finding words, focusing, concentrating, or memory impairment.[23] It also requires a composite T-score less than 45 (a half standard deviation below the normative mean) on the SF-36.[23] Extended follow-up revealed a subset of patients who do not meet this definition at the six-month visit, but do meet the definition if applied at one year. Therefore, in order to capture all PTLDS patients, we applied an expanded version of this definition by extending the time to include the one-year visit.

Cytokine Detection.
The Bio-Plex™ bead array system, and manufacturer recommended, previously described protocols[24] were employed to perform multiplex analysis of fifty-eight cytokines and chemokines, and nine acute phase markers. However, due to inter-batch variation three were dropped, resulting in six acute phase markers. Data processing was completed using Bio-Plex™ manager software (version 5.0). Data normalization between two run batches was achieved by setting all values less than 1 pg/mL to 1 pg/mL, calculating the 10% trimmed mean of each batch, and then multiplying by a factor to equalize the trimmed mean values. The protocol and data generated were MAIME compliant and were deposited in the Gene Expression Omnibus Repository. The cytokines, chemokines and inflammatory markers measured were described in a recent publication [21] and are listed in Table 5. Microarray data will be submitted to a public repository.

Statistical Analyses.
Group comparisons were performed using nonparametric Wilcoxon rank sum or Kruskal-Wallis tests for continuous variables, while chi-square or Fisher's exact tests were used for dichotomous variables. Negative binomial regression was used for number of symptoms. All statistical calculations were performed with SAS 9.3 (SAS Institute, Cary, N.C.). Relative risks and associated confidence intervals were calculated by hand using the standard formulas.

For descriptive analyses of the multiplex data, values were analyzed using the "ratio to average," logged. For subgroup comparisons, "ratio to average" values were analyzed by SAM (Significance Analysis of Microarrays Version 4.0) [22] and sorted based on false discovery rates (FDRs, represented by the q value) to identify cytokine or acute phase proteins with the greatest differences between patient subgroups. Hierarchical clustering software Cluster 3.0 was used to arrange results, which were displayed using Java Treeview (Version 1.1.5r2).

Results

Cohort Characteristics.

Table 5 shows demographic characteristics of our sample of 76 early Lyme patients and 26 healthy controls. There were no statistically significant differences between the total sample of Lyme patients and controls on any of the demographic variables examined, with the exception of years of education which was borderline significant (p=0.05). The PTLDS definition [23] was applied to our cohort of 76 Lyme patients. Eleven (14.5%) met criteria at either six or twelve months (PTLDS group), 29 (38.2%) met the symptom but not the functional impact criteria (Symptom group), and 36 (47.3%) reported neither new symptoms nor decreased daily function and were considered returned to their pre-morbid health (Return to Health group). There were no statistically significant differences found by group on any of the demographic variables examined (Table 5). Similarly, the three clinical outcome groups (PTLDS, Symptoms, and Return to Health) did not differ significantly on any of the clinical variables measured at baseline (Table 6). However, at the 3-month, 6-month, and 1 year follow-up visits, significant differences were found in number of reported symptoms among the PTLDS and Symptom groups compared to the Return to Health group.

Immune Mediator Analysis.

Figure 7A:
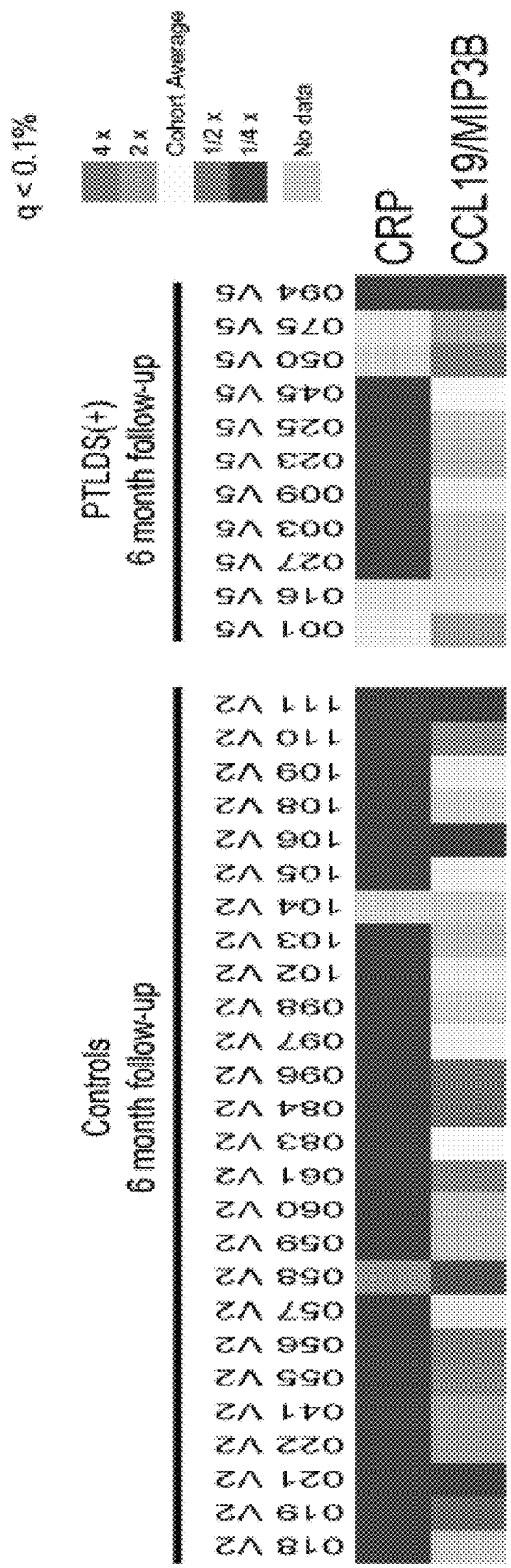
FIG. 7A-7B. CCL19 Identified as an Immune Mediator in PTLDS. Serum samples from patients with diagnosed acute Lyme disease and healthy controls were assayed for the presence of soluble mediators using an optimized multiplex-based assay system. Results are displayed as a heat map to visualize differences in mediator levels.
Figure 7B:
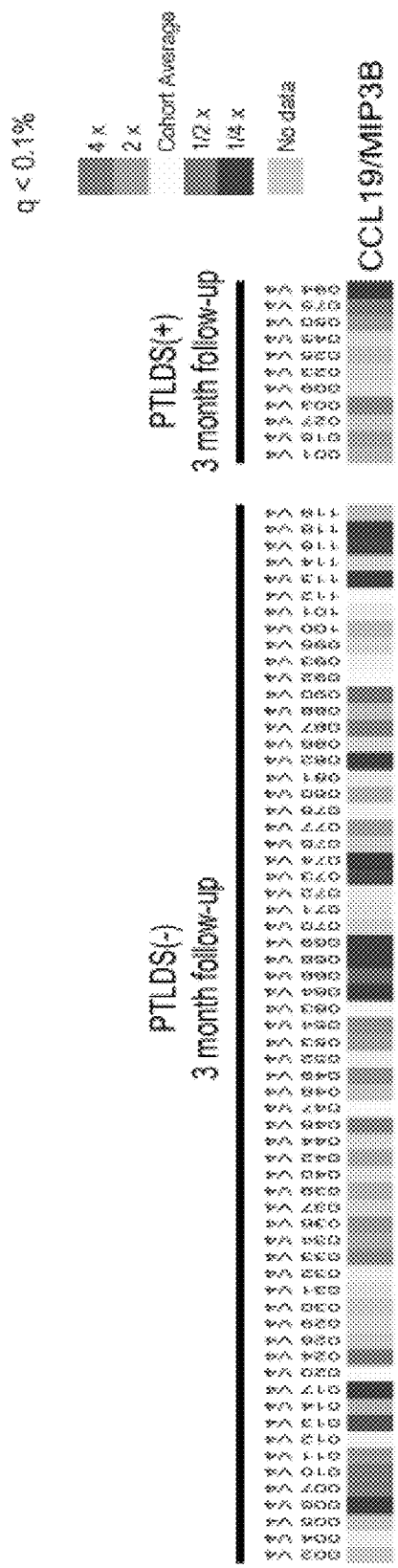

Analysis using SAM showed evidence that among the 65 mediators examined (see Table 7 for a complete list), CCL19 remained consistently elevated in the sera of patients with PTLDS at multiple time points after antibiotic treatment. FIG. 7a shows that only CCL19 and CRP levels were significantly different in PTLDS patients compared to controls at 6 months following treatment completion, at the time of group status determination. When previous visits were examined, we found that only CCL19 levels were significantly different between the PTLDS group compared to controls at 3 months post-treatment (FIG. 7b). Therefore, we focused the remaining analyses presented in this paper on CCL19 levels.

CC119 Levels in Post-Treatment Lyme Disease Syndrome.

Figure 8:
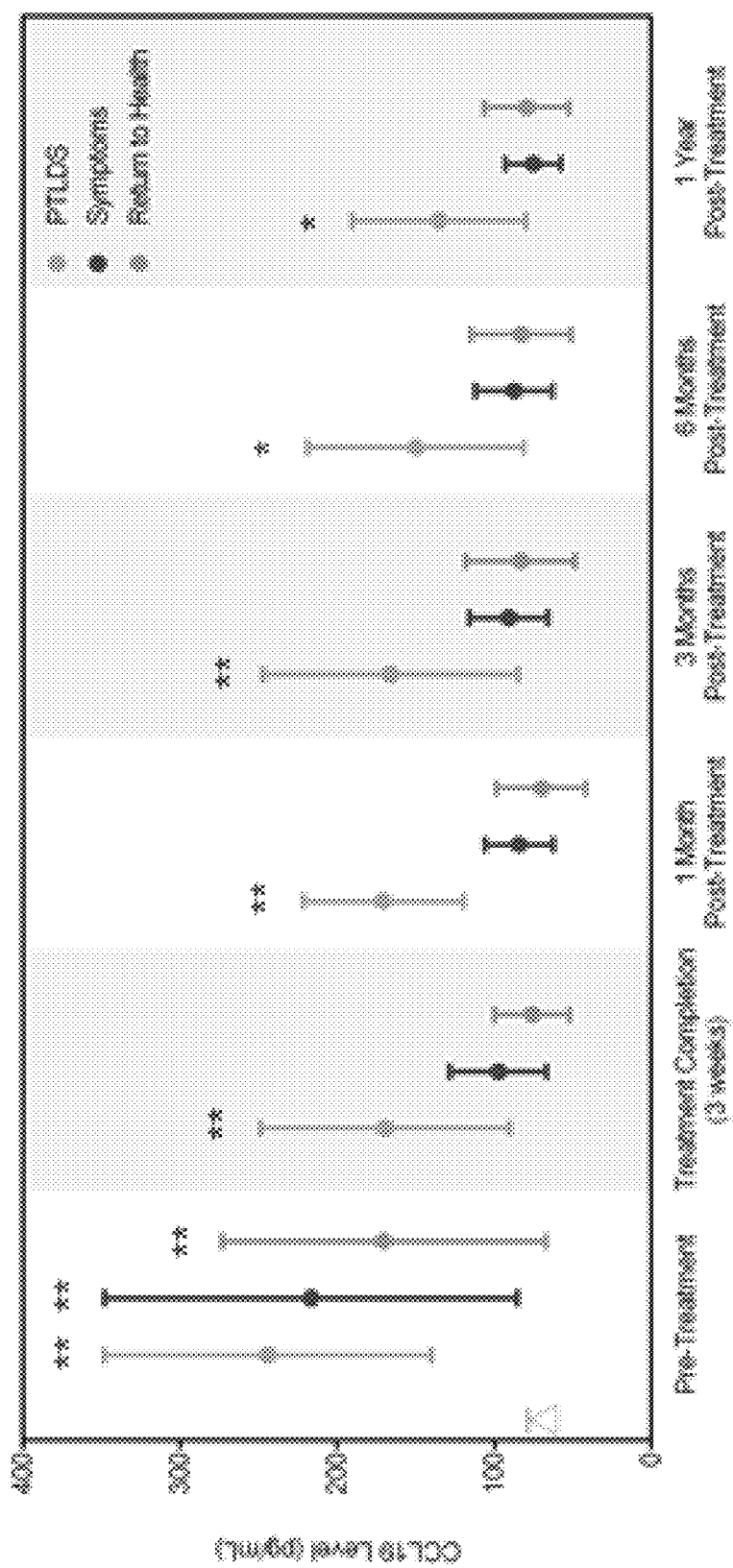
FIG. 8. CCL19 levels are elevated in Lyme disease cases with PTLDS defined at 6 or 12 months follow-up. Displayed are the median and IQR serum levels of CCL19 (pg/mL) among Lyme patients (n=76) over time. Lyme-exposed patients are divided into PTLDS, symptom, and return to health subgroups based on self-reported symptoms and survey measurements at six months and one-year post-treatment. The median control value (79.3 pg/mL) is represented by a triangle; * $p \leq 0.05$, ** $p \leq 0.01$ for comparison of each group to controls.

FIG. 8 shows the median CCL19 levels over time by clinical outcome group. At the time of acute infection, the three Lyme-exposed groups had similar serum CCL19 levels, and all were significantly different from controls (p<0.01 for each). However, at the end of treatment three weeks later, the median serum CCL19 level of the PTLDS group remained significantly different from control group levels while the Symptom and Return to Health groups did not. The persistent elevations in CCL19 level among PTLDS patients were found at each of the subsequent follow-up visits compared to controls (p≤0.05 at each).

To determine if PTLDS outcome status at 6 months post-treatment could be predicted at earlier study visits, we selected a cutoff of 2 standard deviations above the control group mean (182 pg/mL). Using this cutoff, Lyme patients with a CCL19 level ≥182 pg/mL at the end of three weeks of treatment had a 6.83 (95% CI: 2.35-17.29) times greater risk of meeting criteria for PTLDS at 6 months. Similarly, Lyme patients with a CCL19 level of ≥182 pg/mL 1 month after the end of treatment had a 7.5 (95% CI: 3.07-18.33) times increased risk.

Clinical Predictors of CCL19 Level.

The demographic and clinical variables in Tables 5 and 6 (including outcome group) were examined in separate univariate analyses, and four were found to be associated with higher CCL19 level at the baseline visit; a higher number of reported symptoms, female sex, presence of disseminated lesions, and seropositivity. Table 8 shows results of a multiple linear regression using these four variables as predictors of CCL19 level. Disseminated EM lesions was found to be a non-significant predictor and was removed from the final model (Model 2: F=10.51, p<0.0001, adjusted $R^2$=0.28).

This analysis was repeated at the six month follow-up visit to determine if these variables remained predictive of CCL19 level at a later time point (Table 8). While female sex remained significantly associated with CCL19 level in univariate analysis, number of reported symptoms and seropositivity were replaced by duration of illness prior to treatment and outcome status in the model. The effect of female sex was found to be non-significant in multivariate analysis however, and was dropped from the final model (Model 2: F=8.84, p=0.0004, adjusted $R^2$=0.18).

TABLE 5

Demographic Characteristics of Lyme Disease Subgroups and Controls[a]

| | Lyme Disease Patients | | | | Healthy Controls (n = 26) |
|---|---|---|---|---|---|
| | PTLDS (n = 11) | Symptoms (n = 29) | Return to Health (n = 36) | Total (n = 76) | |
| Female Sex | 72.7% | 43.5% | 41.7% | 48.7% | 53.9% |
| Age | 43 | 54 | 53 | 53 | 57 |
| | (29-53) | (46-66) | (34-62) | (38-63) | (46-66) |
| | [20-64] | [20-75] | [20-77] | [20-77] | [22-73] |
| Non-Hispanic, White | 81.8% | 96.6% | 94.4% | 93.4% | 88.5% |
| Years of Education | 16 | 16 | 16 | 16 | 18 |
| | (12-18) | (15-18) | (16-19) | (15-18) | (16-20) |
| | [11-21] | [12-21] | [12-21] | [11-21] | [12-26] |
| Household Income, Thousands[b] | 80 | 125 | 100 | 100 | 125 |
| | (334-110) | (93-150) | (70-150) | (75-150) | (78-165) |
| | [27-250] | [50-500] | [33-500] | [27-500] | [50-350] |

[a]Data are n(%) for categorical variables, median (IQR) [Range] for continuous and count variables.
[b]Eleven participants missing income data; 2 from PTLDS group, 3 from Symptoms group, 4 from Return to Health group, 2 from Control group.

TABLE 6

Clinical Characteristics of Lyme Disease Subgroups[a]

| | PTLDS (n = 11) | Symptoms (n = 29) | Return to Health (n = 36) | Total (n = 76) | p |
|---|---|---|---|---|---|
| Physician-Documented EM | 100.0% | 100.0% | 100.0% | 100.0% | NS |
| Disseminated Lesions Present | 9.1% | 34.5% | 36.1% | 31.6% | NS |
| Time from first symptom to initiation of treatment, days | 6 | 7 | 5 | 7 | NS |
| | (3-10) | (5-10) | (3-14) | (4-11) | |
| | [3-42] | [1-35] | [2-35] | [1-42] | |

TABLE 6-continued

Clinical Characteristics of Lyme Disease Subgroups[a]

| | PTLDS (n = 11) | Symptoms (n = 29) | Return to Health (n = 36) | Total (n = 76) | p |
|---|---|---|---|---|---|
| Sero-positive[b] | 45.5% | 74.1% | 72.2% | 68.9% | NS |
| | 54.6% | 25.9% | 27.8% | 31.1% | |
| Number of Symptoms | | | | | |
| Pre-Treatment Baseline | 12 (10-15) [4-19] | 10 (6-16) [0-22] | 9 (6-12) [1-17] | 9 (6-14) [0-22] | NS |
| Post-Treatment Follow-Up[c] | 17 (8-21) [4-24] | 13 (8-18) [4-24] | 10 (8-12) [3-24] | 11 (8-17) [3-24] | NS |
| 1-Month Follow-Up[d] | 10 (2-14) [0-24] | 3 (1-7) [0-22] | 4 (0-6) [0-15] | 4 (1-8) [0-24] | NS |
| 3-Month Follow-Up[e,f] | 7** (2-12) [1-22] | 3 (1-6) [0-21] | 1 (0-3) [0-15] | 2 (1-6) [0-22] | 0.005 |
| 6-Month Follow-Up[f] | 6** (3-9) [1-23] | 4** (3-7) [0-19] | 2 (0-3) [0-10] | 3 (1-6) [0-23] | 0.0003 |
| 1-Year Follow-Up[f,g] | 13*** (8-19) [6-34] | 4*** (3-10) [0-16] | 1 (0-3) [0-12] | 3 (0-8) [0-34] | 0.0001 |

[a]Data are n(%) for categorical variables, median (IQR) [Range] for continuous and count variables.
[b]Interpreted according to CDC guidelines for two-tier ELISA and reflex WB (IgG/IgM) testing. Two symptom group participants missing complete two-tier serologic data
[c]One patient missing symptom data from Symptoms group
[d]Three patients missing symptoms data; 1 from Symptoms group, 2 from Return to Health group
[e]Two patients missing symptom data from Return to Health group
[f]In post-hoc analysis; *p ≤ 0.05, p ≤ 0.01 and *p ≤ 0.001 for comparison to Return to Health Group
[g]One patient missing symptom data from PTLDS group

TABLE 7

Cytokines, Chemokines, and Inflammatory Markers Measured Using the Bio-Plex ™ Bead Array System

| Growth factors | b-NGF, FGF basic, HGF, PDGF-bb, SCGF-b, VEGF |
|---|---|
| Chemokines | CCL17, CCL19, CTACK, Eotaxin, GROa, IP-10, MCP-1(MCAF), MCP-3, MIG, MIP-1a, MIP-1b, RANTES, SDF-1a |
| Cytokines | G-CSF, GM-CSF, IFN-a2, IFN-g, IL-10, IL-12(p70), IL-12p40, IL-13, IL-15, IL-16, IL-17A, IL-17F, IL-18, IL-1a, IL-1B, IL-1ra, IL-2, IL-21, IL-22, IL-23, IL-25, IL-2Ra, IL-3, IL-31, IL-33, IL-4, IL-5, IL-6, IL-7, IL-8, IL-9, LIF, M-CSF, MIF, sCD40L, SCF, TNF-a, TNF-b, TRAIL |
| Acute phase proteins | CRP, ferritin, fibrinogen, procalcitonin, serum amyloid A and tissue plasminogen activator |

TABLE 8

Regression Results for CCL19 Level at Acute Illness and Six Months Post-Treatment

| | Pre-treatment (n = 76) | | Six-months post-treatment (n = 74) | |
|---|---|---|---|---|
| | Model 1[a] | Model 2 | Model 1 | Model 2 |
| Intercept | 14.05 (42.95) | 16.39 (42.85) | 59.20 (11.85) | 62.64 (11.22) |
| Sex (1 = Female) | 133.07 (31.99)*** | 135.64 (31.85)*** | 12.62 (13.75) | d |
| Number of reported symptoms | 6.52 (2.92)* | 6.55 (2.92)* | c | c |
| Pre-treatment two-tier serology (1 = positive) | 101.43 (35.97)** | 111.23 (34.43)** | c | c |
| Erythema migrans rash (1 = multiple) | 32.73 (34.53) | d | c | c |
| Time from first symptom to treatment, days | c | c | 2.08 (0.89)* | 2.26 (0.87)* |
| Outcome group[b] (1 = Symptoms, 2 = PTLDS) | c | c | 25.61 (9.34)** | 27.26 (9.16)** |

TABLE 8-continued

Regression Results for CCL19 Level at Acute Illness and Six Months Post-Treatment

|  | Pre-treatment (n = 76) | | Six-months post-treatment (n = 74) | |
| --- | --- | --- | --- | --- |
|  | Model 1[a] | Model 2 | Model 1 | Model 2 |
| R-squared | 0.32 | 0.31 | 0.21 | 0.20 |
| Adjusted R-Squared | 0.28 | 0.28 | 0.18 | 0.18 |

*Presented as parameter estimate (standard error).
[b]Defined as PTLDS, Symptom, and Return 1 Health Groups.
c Not significant in univariate analyses
d Removed from model 2
*p ≤ 0.05,
**p ≤ 0.01,
***p ≤ 0.001

DISCUSSION

In this study, the specific molecular finding of elevations in the T-cell chemokine CCL19 both immediately following treatment and at six and twelve months post-treatment is associated with functionally significant, persistent symptoms at six and twelve months after treatment of acute Lyme disease, and that it distinguishes those with PTLDS from those without functionally significant symptoms. While CCL19 levels were elevated in most Lyme disease patients at the time of diagnosis, they frequently remained elevated immediately after completion of antibiotic therapy among those with the later clinical phenotype of PTLDS, as identified by structured questionnaires and validated instruments. Individuals with early Lyme disease who are ideally treated have a greater than 7-fold higher risk of developing PTLDS by six or twelve months post-treatment if their CCL19 level is higher than 182 pg/ml at one month post-treatment. Lyme disease patients who return to normal health or have symptoms without associated functional impact show a pattern of initial CCL19 elevation followed by a return to control levels after treatment, suggesting that CCL19 is specifically linked to PTLDS and is not a feature of mild subjective symptoms.

In a previous study, we examined serum levels of sixty-five immune mediators among forty-four patients with acute Lyme disease and identified a clear associated signature relative to normal controls, including increased CXCL9, CXCL10, and CCL19.[21] In the current study, we confirm the relevance of CCL19 during acute infection but also in the immediate and later post-treatment phase in an expanded cohort of seventy-six patients. CCL19 (and the related chemokine CCL21) is largely produced by reticular stromal cells localized to secondary lymphoid tissues and functions to attract and position CCR7+ T cells, B cells, and dendritic cells to establish an optimal microenvironment for immune response generation.[26, 27] The expression of CCL19 is thought to be constitutive, but activated dendritic cells produce high levels of CCL19 in order to increase immune cell trafficking in secondary lymphoid organs during active immune responses. This is likely responsible for the elevated levels of CCL19 and other immune mediators seen during acute Lyme disease.[21] Consistent with this, in the mouse model of Lyme disease, CCL19 mRNA expression is increased in the lymph nodes of acutely infected mice.[28] Elevated levels of CCL19 have also been observed during states of immune-mediated inflammation including HIV infection, systemic lupus erythematosus, and rheumatoid arthritis.[29-32]

The origin of persistent CCL19 levels among PTLDS patients is less clear, as patients do not display signs of ongoing immune-mediated processes, such as joint synovitis. Interestingly, high CCL19 expression has been found at sites of localized immune-driven reactions where ectopic lymphoid cell accumulation occurs, including the liver during chronic hepatitis C infection, the synovium in rheumatoid arthritis, the salivary glands in Sjogren's syndrome, and in spinal fluid from patients with central nervous system inflammation, including that induced by Lyme neuroborreliosis.[33-39] Based on this, we speculate that elevated CCL19 levels may reflect an ongoing, immune-driven reaction at sites distal to secondary lymphoid tissue. The observation that patients with PTLDS are defined by musculoskeletal pain, behavioral, and neurological symptoms, suggests that the central nervous system may be a site for ectopic immune activity in PTLDS.

It has recently been reported that serum IL-23 levels are elevated during acute disease in patients that develop PTLDS, and proposed that Th-17 mediated immune responses may play a role in PTLDS.[40] While we have not directly addressed the role of the Th-17 effector pathways in our longitudinal cohort, it has been previously shown that CCL19, along with IL-23, drive the development of pathogenic Th-17 cells in a murine model of encephalomyelitis.[41] Therefore CCL19 and IL-23 may identify an informative immune pathway.

Our findings raise the question of whether symptoms such as fatigue, cognitive complaints and mood changes [42, 43] may be related to a cytokine/chemokine effect, as has been hypothesized in other illnesses such as hepatitis-associated fatigue[44] and multiple sclerosis-associated depression.[45] If so, a range of disease management approaches may be helpful to patients and physicians. Medications used to treat depression may decrease cytokine levels and have been hypothesized to reverse symptoms induced by interferon alpha administration.[46] The impact of short-term antibiotic retreatment in this high-risk group has yet to be formally tested, although it has been employed in antibiotic treatment trials of early Lyme disease and may be widely applied in clinical practice.[25, 47]

Previous studies have indicated that initial severity of illness may be predictive of persistent symptoms, suggesting that the biology of early infection may contain information related to long-term outcomes.[14] We extend this observation to molecular findings in the early post-treatment period as well, as post-treatment CCL19 elevations predicted long-term illness outcomes at six and twelve months. Furthermore, we found that CCL19 levels at one month post-treatment were more strongly predictive than those measured at treatment completion. This suggests that a heightened immune-mediated response in the immediate post-treatment period is linked to longer-term symptom persistence.

There is strong evidence supporting the efficacy of behavioral interventions for pain and fatigue management[48, 49] and cognitive rehabilitation[50] in a variety of medical populations that may be applicable to patients with PTLDS. When such targeted symptom management and/or psychological interventions are offered early in the recovery process, individuals with early Lyme disease may have a chance to learn how to adapt and adjust to persistent symptoms, thus helping to reduce interference with daily life functioning and possibly stave off emotional adjustment issues. Classifying immunologic risk factors associated with the development of PTLDS may provide opportunities to identify those at risk earlier than the current six month proposed case definition [11] and to provide closer follow up, education, and early pharmacologic and behavioral interventions.

Clearly, the relationship between PTLDS and elevated CCL19 needs to be validated. Study criteria limiting enrollment to those patients with EM and excluding those with pre-existing conditions marked by subjective symptoms similar to PTLDS (such as fibromyalgia, chronic fatigue syndrome, or depression) may limit generalizability. Further, a different *Borrelia* species is associated with Eurasian Lyme disease; therefore our results need to be tested in other geographic populations. Despite these limitations, the current study offers a foundational finding on how the immunologic response may contribute to clinical observations, and identifies early post-treatment elevations of CCL19 levels as a potential risk factor for PTLDS. This presents an opportunity not only to better understand the pathophysiology of PTLDS, but also to design early interventions for disease management. For example, patients found to have persistent elevation in CCL19 after an initial standard course of antibiotic therapy (typically 2-3 weeks) may be candidates for repeat or extended courses of additional antibiotics.

CONCLUSIONS

The current study identifies early post-treatment elevated CCL19 as a potential risk factor for PTLDS. The origin of persistently elevated CCL19 levels among PTLDS patients is unknown; however, we speculate that it may reflect an ongoing, immune-driven reaction at sites distal to secondary lymphoid tissue. The ability to identify a potential immunologic risk factor for PTLDS provides the opportunity to better understand the pathophysiology of PTLDS, identify those at risk, and to develop early interventions to improve long term outcomes.

REFERENCES

1. Stanek G, Wormser G P, Gray J, Strle F: Lyme borreliosis. Lancet 2012, 379:461-473.
2. Hinckley A F, Connally N P, Meek J I, Johnson B J, Kemperman M M, Feldman K A, White J L, Mead P S: Lyme Disease Testing by Large Commercial Laboratories in the United States. Clin Infect Dis 2014.
3. Tugwell P, Dennis D T, Weinstein A, Wells G, Shea B, Nichol G, Hayward R, Lightfoot R, Baker P, Steere A C: Laboratory evaluation in the diagnosis of Lyme disease. Ann Intern Med 1997, 127:1109-23.
4. Brownstein J S, Holford T R, Fish D: Effect of Climate Change on Lyme Disease Risk in North America. Ecohealth 2005, 2:38-46.
5. Wormser G P: Early Lyme Disease. N Engl J Med 2006, 354:2794-2801.
6. Eshoo M W, Crowder C C, Rebman A W, Rounds M a, Matthews H E, Picuri J M, Soloski M J, Ecker D J, Schutzer S E, Aucott J N: Direct molecular detection and genotyping of *Borrelia burgdorferi* from whole blood of patients with early Lyme disease. PLoS One 2012, 7:e36825.
7. Liveris D, Schwartz I, McKenna D, Nowakowski J, Nadelman R, Demarco J, Iyer R, Bittker S, Cooper D, Holmgren D, Wormser G P: Comparison of five diagnostic modalities for direct detection of *Borrelia burgdorferi* in patients with early Lyme disease. Diagn Microbiol Infect Dis 2012, 73:243-245.
8. Imai D M, Feng S, Hodzic E, Barthold S W: Dynamics of connective-tissue localization during chronic *Borrelia burgdorferi* infection. Lab Investig 2013, 93:900-10.
9. Steere A C, Schoen R T, Taylor E: The clinical evolution of Lyme arthritis. Ann Intern Med 1987, 107:725-731.
10. Strle K, Shin J J, Glickstein L J, Steere A C: Association of a Toll-like receptor 1 polymorphism with heightened Th1 inflammatory responses and antibiotic-refractory Lyme arthritis. Arthritis Rheum 2012, 64:1497-507.
11. Wormser G P, Dattwyler R J, Shapiro E D, Halperin J J, Steere A C, Klempner M S, Krause P J, Bakken J S, Strle F, Stanek G, Bockenstedt L, Fish D, Dumler J S, Nadelman R B: The clinical assessment, treatment, and prevention of lyme disease, human granulocytic anaplasmosis, and babesiosis: clinical practice guidelines by the Infectious Diseases Society of America. Clin Infect Dis 2006, 43:1089-1134.
12. Aucott J N, Rebman A W, Crowder L a, Kortte K B: Post-treatment Lyme disease syndrome symptomatology and the impact on life functioning: is there something here? Qual Life Res 2013, 22:75-84.
13. Shadick N A, Phillips C B, Logigian E L, Steere A C, Kaplan R F, Berardi V P, Duray P H, Larson M G, Wright E A, Ginsburg K S, Katz J N, Liang M H: The long-term clinical outcomes of Lyme disease. A population-based retrospective cohort study. Ann Intern Med 1994, 121: 560-567.
14. Nowakowski J, Nadelman R B, Sell R, McKenna D, Cavaliere L F, Holmgren D, Gaidici A, Wormser G P: Long-term follow-up of patients with culture-confirmed Lyme disease. Am J Med 2003, 115:91-96.
15. Kalish R A, Kaplan R F, Taylor E, Jones-Woodward L, Workman K, Steere A C: Evaluation of study patients with Lyme disease, 10-20-year follow-up. J Infect Dis 2001, 183:453-460.
16. Shapiro E D, Dattwyler R, Nadelman R B, Wormser G P: Response to meta-analysis of Lyme borreliosis symptoms. Int J Epidemiol 2005, 34:1437-9; author reply 1440-3.
17. Embers M E, Barthold S W, Borda J T, Bowers L, Doyle L, Hodzic E, Jacobs M B, Hasenkampf N R, Martin D S, Narasimhan S, Phillippi-Falkenstein K M, Purcell J E, Ratterree M S, Philipp M T: Persistence of *Borrelia burgdorferi* in rhesus macaques following antibiotic treatment of disseminated infection. PLoS One 2012, 7:e29914.
18. Bockenstedt L K, Gonzalez D G, Haberman A M, Belperron A A: Spirochete antigens persist near cartilage after murine Lyme borreliosis therapy. J Clin Invest 2012, 122:2652-60.

19. Shen S, Shin J J, Strle K, McHugh G, Li X, Glickstein L J, Drouin E E, Steere A C: Treg cell numbers and function in patients with antibiotic-refractory or antibiotic-responsive Lyme arthritis. Arthritis Rheum 2010, 62:2127-37.
20. Chandra A, Wormser G P, Klempner M S, Trevino R P, Crow M K, Latov N, Alaedini A: Anti-neural antibody reactivity in patients with a history of Lyme borreliosis and persistent symptoms. Brain Behav Immun 2010, 24:1018-1024.
21. Soloski M, Crowder L, Lahey L, Wagner C, Robinson W, Aucott J, (in press): Serum Inflammatory Mediators as Markers of Human Lyme Disease Activity. PLoS One 2014.
22. Tusher V G, Tibshirani R, Chu G: Significance analysis of microarrays applied to the ionizing radiation response. Proc Natl Acad Sci USA 2001, 98:5116-21.
23. Aucott J N, Crowder L A, Kortte K B: Development of a foundation for a case definition of post-treatment Lyme disease syndrome. Int J Infect Dis 2013, 17:e443-9.
24. Deane K D, O'Donnell C I, Hueber W, Majka D S, Lazar A A, Derber L A, Gilliland W R, Edison J D, Norris J M, Robinson W H, Holers V M: The number of elevated cytokines and chemokines in preclinical seropositive rheumatoid arthritis predicts time to diagnosis in an age-dependent manner. Arthritis Rheum 2010, 62:3161-72.
25. Nadelman R B, Luger S W, Frank E, Wisniewski M, Collins J J, Wormser G P: Comparison of cefuroxime axetil and doxycycline in the treatment of early Lyme disease. Ann Intern Med 1992, 117:273-80.
26. Förster R, Davalos-Misslitz A C, Rot A: CCR7 and its ligands: balancing immunity and tolerance. Nat Rev Immunol 2008, 8:362-71.
27. Comerford I, Harata-Lee Y, Bunting M D, Gregor C, Kara E E, McColl S R: A myriad of functions and complex regulation of the CCR7/CCL19/CCL21 chemokine axis in the adaptive immune system. Cytokine Growth Factor Rev 2013, 24:269-83.
28. Hastey C J, Ochoa J, Olsen K J, Barthold S W, Baumgarth N: MyD88- and TRIF-Independent Induction of Type I Interferon Drives Naive B Cell Accumulation but Not Loss of Lymph Node Architecture in Lyme Disease. Infect Immun 2014, 82:1548-58.
29. Bauer J W, Petri M, Batliwalla F M, Koeuth T, Wilson J, Slattery C, Panoskaltsis-Mortari A, Gregersen P K, Behrens T W, Baechler E C: Interferon-regulated chemokines as biomarkers of systemic lupus erythematosus disease activity: a validation study. Arthritis Rheum 2009, 60:3098-107.
30. Bauer J W, Baechler E C, Petri M, Batliwalla F M, Crawford D, Ortmann W A, Espe K J, Li W, Patel D D, Gregersen P K, Behrens T W: Elevated serum levels of interferon-regulated chemokines are biomarkers for active human systemic lupus erythematosus. PLoS Med 2006:e491.
31. Sellam J, Rouanet S, Hendel-Chavez H, Miceli-Richard C, Combe B, Sibilia J, Le Loët X, Tebib J, Jourdan R, Dougados M, Taoufik Y, Mariette X: CCL19, a B cell chemokine, is related to the decrease of blood memory B cells and predicts the clinical response to rituximab in patients with rheumatoid arthritis. Arthritis Rheum 2013, 65:2253-61.
32. Fontaine J, Poudrier J, Roger M: Short communication: persistence of high blood levels of the chemokines CCL2, CCL19, and CCL20 during the course of HIV infection. AIDS Res Hum Retroviruses 2011, 27:655-7.
33. Heydtmann M, Hardie D, Shields P L, Faint J, Buckley C D, Campbell J J, Salmon M, Adams D H: Detailed analysis of intrahepatic CD8 T cells in the normal and hepatitis C-infected liver reveals differences in specific populations of memory cells with distinct homing phenotypes. J Immunol 2006, 177:729-38.
34. Rupprecht T A, Plate A, Adam M, Wick M, Kastenbauer S, Schmidt C, Klein M, Pfister H-W, Koedel U: The chemokine CXCL13 is a key regulator of B cell recruitment to the cerebrospinal fluid in acute Lyme neuroborreliosis. J Neuroinflammation 2009, 6:42.
35. Kowarik M C, Cepok S, Sellner J, Grummet V, Weber M S, Korn T, Berthele A, Hemmer B: CXCL13 is the major determinant for B cell recruitment to the CSF during neuroinflammation. J Neuroinflammation 2012, 9:93.
36. Bombardieri M, Pitzalis C: Ectopic lymphoid neogenesis and lymphoid chemokines in Sjogren's syndrome: at the interplay between chronic inflammation, autoimmunity and lymphomagenesis. Curr Pharm Biotechnol 2012, 13:1989-96.
37. Pickens S R, Chamberlain N D, Volin M V, Pope R M, Mandelin A M, Shahrara S: Characterization of CCL19 and CCL21 in rheumatoid arthritis. Arthritis Rheum 2011, 63:914-22.
38. Columba-Cabezas S, Serafini B, Ambrosini E, Aloisi F: Lymphoid chemokines CCL19 and CCL21 are expressed in the central nervous system during experimental autoimmune encephalomyelitis: implications for the maintenance of chronic neuroinflammation. Brain Pathol 2003, 13:38-51.
39. Timmer T C G, Baltus B, Vondenhoff M, Huizinga T W J, Tak P P, Verweij C L, Mebius R E, van der Pouw Kraan T C T M: Inflammation and ectopic lymphoid structures in rheumatoid arthritis synovial tissues dissected by genomics technology: identification of the interleukin-7 signaling pathway in tissues with lymphoid neogenesis. Arthritis Rheum 2007, 56:2492-502.
40. Strle K, Stupica D, Drouin E E, Steere A C, Strle F: Elevated levels of IL-23 in a subset of patients with post-lyme disease symptoms following erythema migrans. Clin Infect Dis 2014, 58:372-80.
41. Kuwabara T, Ishikawa F, Yasuda T, Aritomi K, Nakano H, Tanaka Y, Okada Y, Lipp M, Kakiuchi T: CCR7 ligands are required for development of experimental autoimmune encephalomyelitis through generating IL-23-dependent Th17 cells. J Immunol 2009, 183:2513-21.
42. Kaplan R F, Meadows M E, Vincent L C, Logigian E L, Steere A C: Memory impairment and depression in patients with Lyme encephalopathy: comparison with fibromyalgia and nonpsychotically depressed patients. Neurology 1992, 42:1263-7.
43. Hassett A L, Radvanski D C, Buyske S, Savage S V, Gara M, Escobar J I, Sigal L H: Role of psychiatric comorbidity in chronic Lyme disease. Arthritis Rheum 2008, 59:1742-1749.
44. Thompson M E, Barkhuizen A: Fibromyalgia, hepatitis C infection, and the cytokine connection. Curr Pain Headache Rep 2003, 7:342-7.
45. Pucak M L, Carroll K A L, Kerr D A, Kaplin A I: Neuropsychiatric manifestations of depression in multiple sclerosis: neuroinflammatory, neuroendocrine, and neurotrophic mechanisms in the pathogenesis of immune-mediated depression. Dialogues Clin Neurosci 2007, 9:125-39.
46. Capuron L, Gumnick J F, Musselman D L, Lawson D H, Reemsnyder A, Nemeroff C B, Miller A H: Neurobehavioral effects of interferon-alpha in cancer patients: phenomenology and paroxetine responsiveness of symptom dimensions. Neuropsychopharmacology 2002, 26:643-52.
47. Massarotti E M, Luger S W, Rahn D W, Messner R P, Wong J B, Johnson R C, Steere a C: Treatment of early Lyme disease. Am J Med 1992, 92:396-403.
48. Staud R: Treatment of fibromyalgia and its symptoms. Expert Opin Pharmacother 2007, 8:1629-42.
49. Stanos S, Houle T T: Multidisciplinary and interdisciplinary management of chronic pain. Phys Med Rehabil Clin N Am 2006,17:435-50, vii.
50. Cicerone K D, Langenbahn D M, Braden C, Malec J F, Kalmar K, Fraas M, Felicetti T, Laatsch L, Harley J P, Bergquist T, Azulay J, Cantor J, Ashman T: Evidence-based cognitive rehabilitation: updated review of the literature from 2003 through 2008. Arch Phys Med Rehabil 2011:519-30.

We claim:

1. A method for treating a patient likely to develop post-treatment Lyme disease syndrome (PTLDS) and who is currently undergoing a first course of antibiotic treatment for Lyme disease comprising the step of prescribing or administering a second course of antibiotic treatment to a patient who is determined to have an increased level of CCL19 as compared to a control after completing a first course of antibiotics for Lyme disease.

2. The method of claim 1, wherein the second course of antibiotics comprises an antibiotic that is different from the first course of antibiotics.

* * * * *